US008536385B2

(12) United States Patent
Okuyama et al.

(10) Patent No.: US 8,536,385 B2
(45) Date of Patent: Sep. 17, 2013

(54) PROCESS FOR PREPARING DIMETHYL ETHER AND PROCESS FOR PREPARING A MIXTURE OF DIMETHYL ETHER AND METHANOL

(75) Inventors: Keiichi Okuyama, Kawasaki (JP); Yotaro Ohno, Tokyo (JP); Takashi Ogawa, Tokyo (JP); Seiji Aoki, Tokyo (JP); Tsutomu Shikada, Kawasaki (JP); Yasuhiro Mogi, Kawasaki (JP); Toshifumi Suzuki, Kawasaki (JP); Yasuo Miyoshi, Kawasaki (JP); Nobuaki Kobayashi, Tokyo (JP); Kazuro Suzuki, Tokyo (JP)

(73) Assignees: Inpex Corporation, Tokyo (JP); Japan Petroleum Exploration Co., Ltd., Tokyo (JP); Total Gas & Power Ventures, Courbevoie (FR); Toyota Tsusho Corporation, Nagoya-shi (JP)

(*) Notice: Subject to any disclaimer, the term of this patent is extended or adjusted under 35 U.S.C. 154(b) by 0 days.

(21) Appl. No.: 13/370,007

(22) Filed: Feb. 9, 2012

(65) Prior Publication Data
US 2012/0157554 A1 Jun. 21, 2012

Related U.S. Application Data

(62) Division of application No. 12/800,051, filed on May 7, 2010, now abandoned, which is a division of application No. 10/546,221, filed as application No. PCT/JP2004/002795 on Mar. 5, 3004, now abandoned.

(30) Foreign Application Priority Data

| Mar. 6, 2003 | (JP) | 2003-059840 |
| Mar. 6, 2003 | (JP) | 2003-059897 |
| Mar. 6, 2003 | (JP) | 2003-059898 |
| Mar. 6, 2003 | (JP) | 2003-060560 |
| Mar. 4, 2004 | (JP) | 2004-060291 |
| Mar. 4, 2004 | (JP) | 2004-061170 |
| Mar. 4, 2004 | (JP) | 2004-061445 |
| Mar. 4, 2004 | (JP) | 2004-061446 |

(51) Int. Cl.
*C07C 29/15* (2006.01)
*C07C 29/16* (2006.01)

(52) U.S. Cl.
CPC .................... *C07C 29/16* (2013.01)
USPC .......................... 568/909; 568/579

(58) Field of Classification Search
USPC ............ 568/579, 909; 44/448; 585/27
See application file for complete search history.

(56) References Cited

U.S. PATENT DOCUMENTS

| 2,515,845 | A | | 7/1950 | Van Den Bussche et al. |
| 3,954,897 | A | * | 5/1976 | Yamato et al. ............ 585/18 |
| 4,005,986 | A | | 2/1977 | Miyashita et al. |
| 4,665,275 | A | * | 5/1987 | Yoshida et al. ............ 585/27 |
| 4,714,794 | A | * | 12/1987 | Yoshida et al. ............ 585/26 |
| 5,015,404 | A | * | 5/1991 | Kubo et al. ............ 508/132 |
| 5,177,114 | A | | 1/1993 | Van Dijk et al. |
| 5,362,375 | A | * | 11/1994 | Kubo et al. ............ 208/19 |
| 7,015,255 | B1 | * | 3/2006 | Tomura et al. ............ 518/700 |
| 2001/0008621 | A1 | | 7/2001 | Christensen et al. |
| 2003/0055184 | A1 | | 3/2003 | Song et al. |

FOREIGN PATENT DOCUMENTS

| CN | 1249267 A | 4/2000 |
| EP | 0 989 094 A2 | 3/2000 |
| GB | 2 092 172 A | 8/1982 |
| JP | 52-46192 | 11/1977 |
| JP | 58-157896 A | 9/1983 |
| JP | 5-254802 A | 10/1993 |
| JP | 9-131533 A | 5/1997 |
| JP | 10-182531 A | 7/1998 |
| JP | 2000-109437 | * 4/2000 |
| JP | 2000-185904 A | 7/2000 |
| JP | 2002-510272 A | 4/2002 |
| JP | 2002-173304 A | 6/2002 |
| WO | WO 98/46525 A1 | 10/1998 |
| WO | WO 02/38499 A1 | 5/2002 |

OTHER PUBLICATIONS

Ola Olsvik et al., "High Pressure Autothermal Reforming (HP ATR)", *Studies in Surface Science and Catalysis*, vol. 119, pp. 875 to 882, (1998).
International Search Report dated Jun. 15, 2004 for PCT/JP2004/002795.
Office Action dated Mar. 9, 2007 from The Patent Office of the People's Republic of China for application No. 2004800059601.
Office Action dated Jun. 8, 2007 from Australian Patent Office for application No. 2004218098.
Russsian Office Action for application No. 2005130988/15, (2007).
Norwegian Office Action dated Dec. 10, 2012 (along with an English-language translation thereof) for Norwegian Patent Application) No. 20052970.
Christensen T.S., et al., "Improtved syngas production using autothermal reforming," Hydrocarbon Processing, International Edition (1994), 73(3), 39-42, 44, 46.

* cited by examiner

*Primary Examiner* — Johann R Richter
*Assistant Examiner* — Pancham Bakshi
(74) *Attorney, Agent, or Firm* — Holtz Holtz Goodman & Chick PC

(57) ABSTRACT

A process for preparing dimethyl ether or a mixture of dimethyl ether and methanol including passing a raw gas containing carbon monoxide and hydrogen through a catalyst slurry containing a mixture including (a) a medium oil having as a main component, a branched, saturated aliphatic hydrocarbon having 16 to 50 carbon atoms, 1 to 7 tertiary carbon atoms, 0 quaternary carbon atoms, and 1 to 16 carbon atoms in the branched chains bonded to the tertiary carbon atom; and at least one of the tertiary carbon atoms is bonded to hydrocarbon chains with a chain length having 4 or more of carbon atoms in three directions, (b) a methanol synthesis catalyst; (c) a methanol dehydration catalyst; and (d) a methanol shift catalyst or a methanol dehydration/shift catalyst.

10 Claims, 11 Drawing Sheets

PROCESS FOR PREPARING DIMETHYL ETHER AND PROCESS FOR PREPARING A MIXTURE OF DIMETHYL ETHER AND METHANOL

CROSS-REFERENCE TO RELATED APPLICATIONS

This application is a divisional application of application Ser. No. 12/800,051 filed May 7, 2010 (abandoned), which is a divisional application of application Ser. No. 10/546,221 filed Sep. 15, 2005 (abandoned), which is the U.S. national phase application of International Application PCT/JP2004/002795 filed Mar. 5, 2004.

TECHNICAL FIELD

The present invention relates to a method for preparing a synthesis gas containing hydrogen and carbon monoxide as main components, by reforming a gas produced by a partial combustion of a hydrocarbon with a catalyst, and to a method for preparing dimethyl ether using the synthesis gas, in which the synthesis gas is the most suitable one as a synthesis gas of $H_2/CO=0.8$ to 1.2 (molar ratio).

BACKGROUND ART

A synthesis gas containing hydrogen and carbon monoxide is used as a raw material for the synthesis of F-T, methanol, ammonia, or the like.

The synthesis gas is prepared from various organic compounds. It is known that a method for preparing the synthesis gas is a reaction of the organic compound with steam and/or carbon dioxide, a partial oxidation of the organic compound by oxygen and/or air, etc.

In particular, with regard to a gaseous organic compound, the following methods are used: (1) a method of reacting an organic compound with steam and/or carbon dioxide at high temperatures in the presence of a catalyst, (2) a method comprising a partial oxidization of an organic compound with oxygen and/or air to generate heat, with which steam and/or carbon dioxide is/are mixed and reacted in a catalyst layer, and (3) a combination of (1) and (2).

However, the above methods have disadvantages as follows.

In the (1) method, since carbon is produced on a catalyst by decomposing an organic compound at high temperatures, an upper limit of the temperature is given. In the (2) method, an organic compound is rapidly decomposed by oxygen, but the organic compound as a heat source is preferably consumed as little as possible. Therefore, the method preferably requires a low temperature. Further, since in any method of (1) to (3), a reaction which produces carbon on a catalyst from a produced carbon monoxide may also occur, a lower limit of the temperature is given.

In order to solve these problems, the following methods have been disclosed.

As a method for preparing a synthesis gas using a catalyst, for example, Patent Document 1 discloses a process in which a catalyst having suppressed carbon deposition activity is used for the reaction of the unreacted carbon-containing organic compound in the high-temperature mixed gas with carbon dioxide and/or steam. Patent Document 2 discloses a process wherein, with an object of providing a catalyst for production of a synthesis gas by a methane reforming reaction, a high activity catalyst for methane reforming can be obtained by modifying the catalyst by supporting on a carrier or by mixing to the catalyst a specific amount of at least one metal compound selected from platinum group metal elements.

On the other hand, for a method for preparing synthesis gas without a catalyst, Patent Document 3 discloses that the formation temperature is set to about 1000 to 1900° C.

[Patent Document 1]
PCT Japanese Translation Patent Re-Publication No. WO98/46525
[Patent Document 2]
Japanese Unexamined Patent Application Publication No. 9-131533
[Patent Document 3]
Japanese Examined Patent Application Publication No. 52-46192

DISCLOSURE OF THE INVENTION

Problems to be Solved by the Invention

However, in a method of using a catalyst, in the case where $H_2/CO$ in a synthesis gas is decreased to 2 or less, the increase in the carbon dioxide concentration in the produced synthesis gas is not negligible. For example, in a process for synthesizing dimethyl ether using the following reaction formula (1), a synthesis gas having the ratio of 1:1 of hydrogen to carbon monoxide is required, but in a method using a catalyst, the carbon dioxide concentration in the produced synthesis gas reaches 20 to 40% on the dry basis.

$$3H_2 + 3CO \rightarrow CH_3OCH_3 + CO_2 \qquad (1)$$

Carbon dioxide contained in a raw gas inhibits the reaction, so that it adversely affects the manufacturing process. Also, the circulation of a large amount of carbon dioxide in a reaction system is not desired, because it increases the apparatus cost and the operating cost.

In order to prevent these disadvantages, adding a process for removing $CO_2$ from the raw gas may be conceived, but it would result in increase in the apparatus cost and the operating cost.

Also, it is known that in a catalyst layer, carbon is produced by the following reaction, whereby a pressure drop in the catalyst layer is increased, and also the activity of the catalyst is lowered due to coverage of the surface of the catalyst, which hinders the operation of the apparatus.

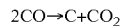

$$2CO \rightarrow C + CO_2$$

When preparing a synthesis gas in which $H_2/CO$ is as low as 1, the concentration of CO in the gas is increased, so that carbon is particularly easily produced.

On the other hand, in a method not using a catalyst, in order not to retain a hydrocarbon which is an intermediate product, or an unreacted organic compound, the reaction temperature tends to become high. The high temperature can be obtained by the combustion of the fuel, but the ratio of the raw material to be converted to $H_2$ and CO to that changing to heat increases, so that the energy efficiency is lowered. In order to increase the energy efficiency, it is also considered that the reaction temperature is decreased. However, if the reaction temperature is decreased, a hydrocarbon including methane or acetylene is formed in the produced gas. The remaining methane lowers the reactivity of the downstream process that uses the synthesis gas, and the remaining acetylene makes it difficult to compress the synthesis gas, and also there is a risk of producing an explosive acetylide in a plant system.

The present invention has been accomplished in the light of the above matters. Hence, an object of the present invention is to provide a method for preparing a synthesis gas that does not contain a hydrocarbon, and lowers the carbon dioxide concentration in the synthesis gas, and method for preparing dimethyl ether using the same.

Means for Solving the Problems

In order to solve the above problems, the present inventors have studied by paying attention to an equilibrium temperature. As a result, the inventors have obtained the following.

If the temperature for reaching an equilibrium state (the outlet temperature of the catalyst layer) is set to 1100 to 1300° C., although the ratio of hydrogen to carbon monoxide is reduced, soot is not produced, and the amount of carbon dioxide as an auxiliary raw material can be also reduced. As a result, using an LNG fuel, it is possible to reduced the carbon dioxide concentration in the produced gas to 10 vol % or less. Using an LPG fuel, it is possible to make the carbon dioxide concentration in the produced gas to 5 vol %. Also, since a catalyst is operated efficiently at high temperatures, a high price catalyst containing noble metals is not required, and the amount of the catalyst may be decreased.

In addition, the inlet temperature of the catalyst layer is decreased by setting the gas retention time in the upstream of the catalyst layer to 2 seconds or more.

The present invention is based on the above knowledge, and has the following characteristics.

The invention described in a first embodiment of the present invention is a method for preparing a synthesis gas having hydrogen and carbon monoxide as main components, which is prepared by reforming a gas with a catalyst, wherein the gas is produced by a partial combustion of hydrocarbons by using a synthesis gas producing furnace in which a catalyst layer is formed in the inside thereof, characterized in that the carbon dioxide concentration in the synthesis gas prepared by setting the outlet temperature of the catalyst layer to 1100 to 1300° C. is 10% or less.

The invention described in a second embodiment of the present invention is characterized in that the gas retention time in the upstream of the catalyst layer is 2 seconds or more.

The invention described in a third embodiment of the present invention is characterized in that after terminating the catalytic reaction, a synthesis gas is rapidly cooled to 600° C. or less.

The invention described in a fourth embodiment of the present invention is a method for preparing dimethyl ether from a synthesis gas containing carbon monoxide and hydrogen, characterized by using the synthesis gas prepared by the method according to any one of the first, second- or third embodiments of the present invention.

The invention described in a fifth embodiment of the present invention is a method for preparing dimethyl ether from a synthesis gas containing carbon monoxide and hydrogen with the ratio of 1:0.8 to 1.2, characterized by using the synthesis gas characterized by using the synthesis gas prepared by the method according to any one of claims 1 to 3.

The invention described in claim 6 is a preparation furnace for preparing a synthesis gas which comprises effusing a raw material, which contains at least a hydrocarbon and an oxidizing agent, from a burner mounted at the top portion of the furnace; partially combusting the hydrocarbon in a space above a catalyst layer formed inside of the furnace; and preparing a synthesis gas containing hydrogen and carbon monoxide in the catalyst layer, characterized in that it has a space to meet the conditions of the following (1) and (2), above the catalyst layer:

(1) $L \geq D/2 \times \cotan \theta_1$, and
(2) Gas retention time in the space is 2 seconds or more wherein L is a height of the space above the catalyst layer, D is an inside diameter of the furnace, $\theta_1$ is a ½ angle of an apex angle in the vertical cross-section of a conical breadth of an effusion flow effused into the inside of the furnace from the burner, which is in the range of $6.5° \leq \theta_1 \leq 9°$.

The invention described in claim 7 is the furnace for preparing a synthesis gas described in claim 6, characterized by further satisfying the condition of (3):

(3) $\theta_2 \geq 25°$ wherein $\theta_2$ is a ½ angle of the apex angle in the vertical cross-section of the conical-shaped top portion of the furnace.

The invention described in an eighth embodiment of the present invention is a furnace for preparing a synthesis gas containing hydrogen and carbon monoxide in a catalyst layer by effusing a raw material containing at least a hydrocarbon and an oxidizing agent from a burner mounted at the top portion of the furnace, and partially combusting the hydrocarbon in a space above the catalyst layer formed inside of the furnace, characterized in that it has a space to meet the conditions of the following (1), (2) and (4), above the catalyst layer:

(1) $L \geq D/2 \times \cotan \theta_1$,
(2) Gas retention time in the space is 2 seconds or more, and
(4) $L \geq 10d$ wherein L is a height of the space above the catalyst layer, D is an inside diameter of the furnace, $\theta_1$ is a ½ angle of an apex angle in the vertical cross-section of a conical breadth of an effusion flow effused into the inside of the furnace from the burner, which is in the range of $6.5° \leq \theta_1 \leq 9°$, and d is a minimum diameter of a circle being capable of covering all the gas effusing holes of the burner.

The invention described in a ninth embodiment of the present invention is a furnace for preparing a synthesis gas containing hydrogen and carbon monoxide in a catalyst layer by effusing a raw material containing at least a hydrocarbon and an oxidizing agent from a burner mounted at the top portion of the furnace, and partially combusting the hydrocarbon in a space above the catalyst layer formed inside of the furnace, characterized in that it has a space to meet the conditions of the following (1), (2), (3) and (5), above the catalyst layer:

(1) $L \geq D/2 \times \cotan \theta_1$,
(2) A gas retention time in the space is 2 seconds or more,
(3) $\theta_2 \geq 25°$, and
(5) $D \geq 3d$ wherein L is a height of the space above the catalyst layer, D is an inside diameter of the furnace, $\theta_1$ is a ½ angle of an apex angle in the vertical cross-section of a conical breadth of an effusion flow effused into the inside of the furnace from the burner, which is in the range of $6.5° \leq \theta_1 \leq 9°$, $\theta_2$ is a ½ angle of the apex angle in the vertical cross-section of the top conical-shaped portion of the furnace, and d is a minimum diameter of a circle being capable of covering all the gas effusing holes of the burner.

The invention described in a tenth embodiment of the present invention is the furnace for preparing a synthesis gas described in the ninth embodiment of the present invention, characterized in that it further satisfies the condition of the following (4):

(4) $L \geq 10d$.

The invention described in an eleventh embodiment of the present invention is the furnace for preparing a synthesis gas according to any one of the sixth, seventh, eighth, ninth or tenth embodiments of the present invention, characterized in that the carbon dioxide concentration in the synthesis gas prepared by setting the outlet temperature of the catalyst layer to 1100 to 1300° C. is 10 vol % or less.

The invention described in a twelfth embodiment of the present invention is the furnace for preparing a synthesis gas described in an eleventh embodiment, characterized in that after terminating the catalytic reaction, the synthesis gas is rapidly cooled to 600° C. or less.

The invention described in a thirteenth embodiment of the present invention is the furnace for preparing a synthesis gas described in any one of the sixth, seventh, eighth, ninth, tenth, eleventh or twelfth embodiments, characterized in that dimethyl ether is prepared from the synthesis gas containing carbon monoxide and hydrogen, which is prepared by the furnace for preparing the synthesis gas.

The invention described in the fourteenth embodiment of the present invention is the furnace for preparing a synthesis gas described in any one of the sixth, seventh, eighth, ninth, tenth, eleventh or twelfth embodiments of the present invention, characterized in that dimethyl ether is prepared from the synthesis gas containing carbon monoxide and hydrogen having the ratio of 1:0.8 to 1.2, which is prepared by the furnace for preparing the synthesis gas.

BEST MODE FOR CARRYING OUT THE INVENTION

<As for a First Invention>

Figure 1:
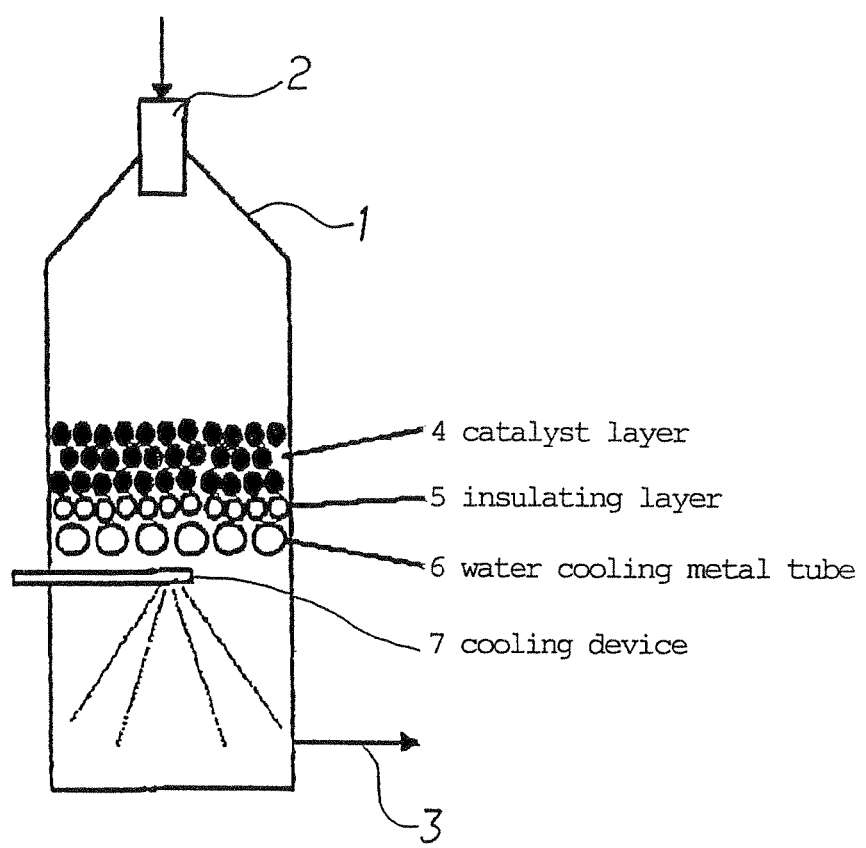
FIG. 1 is a construction diagram showing a furnace for preparing a synthesis gas according to an embodiment of the present invention.

Hereinafter, the present invention will be described in detail with the limitation reasons thereof.

In a conventional process for preparing a synthesis gas, the remainder of an excess carbon dioxide inhibits the reaction, thereby adversely affecting the manufacturing process. First, the results of the investigation to this disadvantage will be described as follows.

For example, in a process for synthesizing dimethyl ether from a raw gas containing carbon monoxide and hydrogen, as represented by the formula (1) below, a synthesis gas having 1:1 of the ratio of hydrogen to carbon monoxide is required.

$$3H_2+3CO \rightarrow CH_3OCH_3+CO_2 \tag{1}$$

However, in the case of preparing a synthesis gas (a mixed gas having mainly (containing) hydrogen and carbon monoxide) from a natural gas or a propane gas as a raw material, generally, the molar ratio of hydrogen/carbon monoxide is 2 or more, thereby the molar ratio of hydrogen/carbon monoxide in the synthesis gas should be decreased in the case of using the synthesis gas in a process for synthesizing dimethyl ether. To decrease the proportion of hydrogen in the synthesis gas, for example, it is effective to increase carbon monoxide by introducing carbon dioxide into the reaction system of the synthesis gas and reacting with hydrogen, according to the following formula (2).

$$H_2+CO_2 \rightarrow CO+H_2O \tag{2}$$

However, since the above reaction (2) is an equilibrium reaction, not all carbon dioxide introduced are reacted, and the unreacted, namely the excess carbon dioxide, remains in a produced synthesis gas. Also, in practice, to make 1:1 of the ratio of hydrogen to carbon monoxide, carbon dioxide is generally added more than the flow rate of a raw gas such as natural gas, etc, whereby the concentration of carbon dioxide contained in the produced synthesis gas reaches 20 to 40% on the dry basis.

Therefore, the present inventors have further investigated to solve the problem of decreasing the carbon dioxide concentration. As a result, they have obtained the following.

A produced synthesis gas contains carbon monoxide, carbon dioxide, hydrogen and water (steam), which maintain an equilibrium by the shift reaction represented by the following reaction formula (3).

$$CO+H_2O=CO_2+H_2 \tag{3}$$

In order to increase carbon monoxide (CO) and decrease hydrogen ($H_2$), it is preferable that the reaction proceeds to the left side of the formula by adding carbon dioxide ($CO_2$) to the reaction system. However, the carbon dioxide concentration in a synthesis gas is increased as described above. On the other hand, since the reaction proceeds to the left at higher temperature and to the right at lower temperature, in order to decrease $H_2$, that is, in order to increase CO, the reaction may be carried out at high temperature. The low ratio of $H_2/CO$ can be realized by elevating the temperature, thereby inhibiting $CO_2$ added to the system and decreasing the concentration of $CO_2$ contained in the produced gas. However, since a catalyst generally has a limiting heat-resistant temperature, the temperature is not raised over that temperature. There is a Ni catalyst that is used generally, but the melting point of Ni is 1455° C., therefore, the maximum temperature for use of a catalyst of fine Ni particles supported on a carrier is 1455° C. or less.

Herein, a synthesis gas according to the present invention is prepared by using a furnace for producing synthesis gas in which a catalyst layer is provided therein. That is, the furnace for producing a synthesis gas is an auto thermal reformer (hereinafter referred to as ATR) in which a gas prepared by a partial combustion of hydrocarbons is reformed by a catalyst, whereby a synthesis gas containing hydrogen and carbon monoxide as main components is prepared. Also, even if the temperature of the synthesis gas obtained is approximately 1000° C., since the inlet temperature of the catalyst layer in the ATR is generally about 1400° C., the ATR is generally operated at 1400° C. or less.

Herein, the present inventors have checked over the temperature difference between an inlet and an outlet of a catalyst layer inside of an ATR. As a result, they found that a gas introduced into the catalyst layer contains methane flown out of a partial combustion region, which is the main cause for the temperature difference between the inlet and outlet of the catalyst layer. That is, methane is reacted with the surrounding $CO_2$ or $H_2O$, and is converted to $CO+H_2$, which is an endothermic reaction. In the case that a gas containing 10% of methane at a temperature of 1400° C. in the inlet of the catalyst layer is decomposed all in the catalyst layer, the outlet temperature of the catalyst layer is about 1000° C. when calculated from an endothermic amount.

And the reaction equilibrium exists in the outlet of a catalyst layer having a sufficient capacity being capable of consuming methane, therefore the $CO_2$ concentration of a produced synthesis gas is decided by this temperature.

As shown above, if lowering the concentration of methane in the inlet of a catalyst layer, it eliminates the temperature difference between the inlet and outlet of the catalyst layer in an ATR, and it is possible to lower the concentration of $CO_2$ in a synthesis gas by elevating the outlet temperature in the catalyst layer while maintaining the inlet temperature in the catalyst layer below the limiting heat-resistant temperature of the catalyst.

And it was found that although the amount of oxygen used for a partial combustion of a hydrocarbon is increased so as to elevate the outlet temperature of the catalyst layer, increase in the inlet temperature of the catalyst layer is less than that of the outlet temperature thereof. That is caused by the decrease in the amount of methane flown out by accelerating the partial combustion reaction due to the increase in the temperature of the region where the partial combustion takes place.

As shown above, in order to decrease the concentration of $CO_2$ contained in a produced gas, the outlet temperature of a catalyst layer is preferably high. However, while it is possible to decrease the concentration of $CO_2$ in the catalyst layer by increasing the outlet temperature of the catalyst layer, the energy efficiency is lowered. Accordingly, to make the concentration of $CO_2$ to be 10% or less in the present invention, the outlet temperature of the catalyst layer is set at 1100 to 1300° C.

Also, in a catalyst layer, it is known that carbon is produced by the following reaction, whereby the pressure drop of the catalyst layer is increased. It is also known that the surface of the catalyst is covered, whereby the activity of the catalyst is lowered, which hinders the operation of the apparatus.

$$2CO \rightarrow C+CO_2$$

Since this reaction is an exothermic reaction, carbon is more easily produced at lower temperature. As for this point (inhibiting the formation of carbon), it is preferable to increase the temperature of the catalyst layer. In practice, by increasing the outlet temperature of the catalyst layer to 1100° C. or more, the formation of carbon on the surface of the catalyst was prevented even in the case of preparing a synthesis gas having $H_2/CO$ ratio of 1, under the reaction condition at about 30 atm.

On the other hand, even in the case of supplying a raw gas so as to set the outlet temperature of the catalyst layer to 1300° C., a hydrocarbon gas such as methane and acetylene remained in a gas introduced in the catalyst layer. As described above, the remaining methane lowers the reactivity in the downstream process that uses the synthesis gas, and the remaining acetylene makes it difficult to compress the synthesis gas, and also there is a risk of producing an explosive acetylide in a plant system. That is, a catalyst is indispensable in this process, whereby it is possible to have a low concentration of $CO_2$ with high-heat efficiency.

As described above, the preparation of a synthesis gas is carried out by setting the temperature that it reaches an equilibrium, that is, the temperature of a catalyst layer (outlet), to 1100 to 1300° C., whereby even in the case of lowering the ratio of oxygen to fuel, soot formation is prevented due to not being in the region of the soot production. In addition, the shift reaction can be controlled by the temperature, and in order to decrease hydrogen ($H_2$), adding a conventional amount of carbon dioxide ($CO_2$) to a reaction system is not required, and the amount of an auxiliary raw material: carbon dioxide can be decreased to obtain a necessary ratio of $H_2/CO$ (for example, the ratio is 1 in the synthesis of DME). As a result, the carbon dioxide concentration in the produced gas in an LNG fuel can be 10 vol % or less. In an LPG fuel, since the ratio of carbon/hydrogen in a molecule is high, it is easy to increase the concentration of CO, and the carbon dioxide concentration can be 5 vol %. In addition, since a catalyst is operated efficiently at high temperatures, a less amount of the catalyst is required.

As described above, in the present invention, in a method for preparing a synthesis gas having hydrogen and carbon monoxide as main components by reforming a gas produced by a partial combustion of a hydrocarbon with a catalyst, the temperature in the catalyst layer is 1100 to 1300° C., and the carbon dioxide concentration in the synthesis gas is 10% or less.

Furthermore, in the present invention, a space is formed in the upstream of the catalyst layer. That is, by producing a sufficient gas retention time, whereby the decomposition reaction of methane is accelerated, the inlet temperature of a catalyst layer has been shown to be further reduced. In the upstream of the catalyst layer, the gas retention time is 2 seconds or more, preferably 3 seconds or more. By securely forming a space in which the gas retention time in the upstream of the catalyst layer is 2 seconds or more, in the case of supplying a raw gas, in which the outlet temperature of the catalyst layer is 1300° C., the inlet temperature of the catalyst layer is controlled to about 1400° C. Furthermore, in a high temperature Ni catalyst, a little sintering occurred, whereby the initial activity thereof was reduced. However, since it is used at a highly reactive high temperature, it gas been shown that a necessary activity is sufficiently maintained for a long duration.

In addition, it is preferable that a synthesis gas obtained by the above reaction is rapidly cooled to 600° C. or less immediately after terminating the catalytic reaction, whereby a gas having the same composition at the outlet of a catalyst layer is passed into a downstream synthesis reaction. Since the reaction rate is reduced at 600° C. or less, whereby the change of the gas composition by the following reaction is almost negligible, the ratio of $H_2/CO$ can be maintained at a predetermined value, and there is no increase of methane or $CO_2$ that inhibit the downstream synthesis reaction.

$$CO+H_2O \rightarrow H_2+CO_2$$

$$CO+3H_2 \rightarrow CH_4+H_2O$$

$$2CO+2H_2 \rightarrow CH_4+CO_2$$

Furthermore, due to passing the obtained synthesis gas rapidly through a temperature region in which the change of the gas composition is not negligible, the rapid cooling is more preferably carried out within 0.1 second after terminating the reaction.

A method for a rapid cooling of a synthesis gas is not particularly limited. For example, there are a method for directly cooling by spraying water to a gas coming out of a catalyst layer and a method for indirectly cooling by a heat exchanger.

FIG. 1 shows an embodiment of a furnace for preparing a synthesis gas.

In this embodiment, an inlet 2 for a raw gas is provided in the upper end of a furnace 1 for preparing a synthesis gas, and an outlet 3 of the synthesis gas is formed at the lower end thereof, and also a catalyst layer 4 is provided inside of the furnace 1 for preparing the synthesis gas.

In the above construction, in the bottom part of the catalyst layer 4, an adiabatic layer 5 for holding the catalyst layer 4 and a water-cooling metal tube 6 are provided in this order. In addition, in this preparation furnace, a cooling means 7 for cooling the produced synthesis gas by performing cooling such as a water-spray, etc. is provided directly underneath the water-cooling metal tube 6. By the above construction, the inside of the preparation furnace is in a compact structure, and also the catalyst layer 4 is held easily by the adiabatic layer 5 and the water-cooling metal tube 6.

According to the furnace for preparing the synthesis gas, the raw gas is introduced inside of the furnace 1 for preparing the synthesis gas through the inlet 2 for the raw gas, which then makes then contact with the catalyst layer 4 in the process of flowing the lower portion of the furnace 1, and a desired synthesis gas is obtained. Thereafter, the synthesis gas makes contact with the adiabatic layer 5, which then makes contact with the water-cooling metal tube 6 and the cooling means 7, and the synthesis gas is rapidly cooled to 600° C. or less. And the synthesis gas having the $CO_2$ concentration of 10% or less is discharged out of the furnace from the outlet 3 of the synthesis gas.

The kind of the catalyst used is not particularly limited if a heat resistance is satisfied at the reaction temperature of 1100 to 1300° C. Examples of the catalyst include a metal such as titanium, vanadium, chromium, manganese, iron, cobalt, nickel, copper, zinc, potassium, yttrium, zirconium, niobium, molybdenum, ruthenium, rhodium, palladium, gold, cadmium, indium, tin, hafnium, tantalum, tungsten, rhenium, osmium, iridium, platinum, silver, mercury, tellurium, lead, bismuth, thallium, uranium, lithium, sodium, potassium, rubidium, cesium, beryllium, magnesium, calcium, strontium, barium, boron, aluminum, scandium, thorium, lead and lanthanoid, an oxide thereof, and the like.

The catalyst can be supported on a carrier. The carrier can be used singly or in a combination of two or more selected from the group consisting of silica, alumina, titania, zirconia, magnesia, zeolite, etc.

The particle size of the catalyst is not particularly limited.

The hydrocarbon of a raw gas may be methane, a hydrocarbon having about 2 to 5 carbon atoms and a mixture thereof, a natural gas, methane prepared from coal and other materials, LPG, etc., and a suitable mixture thereof can be used.

Oxygen can be a pure oxygen, air, etc.

The reactor is not particularly limited. The gas used in the reaction may be a hydrocarbon, oxygen, carbon dioxide gas and steam, in which nitrogen may be included.

As a reaction condition except the temperature of the catalyst layer, the pressure may be in the range of atmospheric pressure to 50 atm, but is not particularly limited.

As described above, the present invention can prepare a synthesis gas not containing any hydrocarbon in the produced synthesis gas and having a low carbon dioxide concentration. And also, due to a low carbon dioxide in the synthesis gas of the present invention, in the case of using a synthesis gas as a raw material in other processes (for example, a process for synthesizing dimethyl ether), the process for removing carbon dioxide is not necessary, and the raw material can be directly supplied to the process as it is. As a result, for example, dimethyl ether can be prepared from the synthesis gas with a higher efficiency.

<As for a Second Invention>

[Technical Field]

The present invention relates to a furnace for preparing a synthesis gas in which a hydrocarbon is reformed to a synthesis gas containing carbon monoxide and hydrogen.

[Background Art]

Generally, a furnace for preparing a synthesis gas, which is referred to as an Auto Thermal Reformer (hereinafter referred to as ATR), is known. In the ATR, temperature is increased by a partial combustion of a hydrocarbon inside of the furnace, whereby carrying out the reformation by heat.

Figure 7:
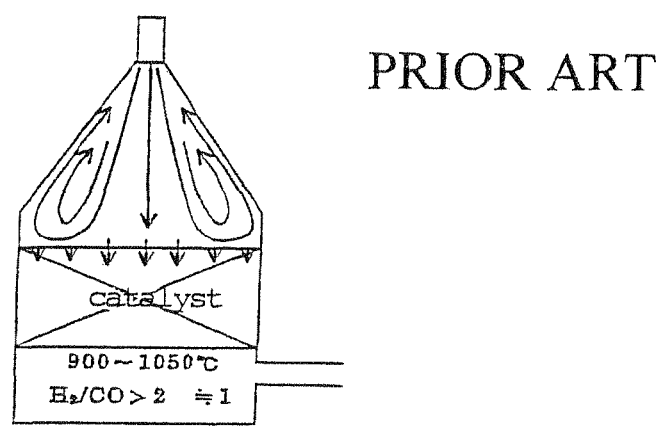
FIG. 7 is a vertical cross-sectional view of a conventional furnace for preparing a synthesis gas.

FIG. 7 shows a cross-sectional view of a conventional ATR. It is considered that in the conventional ATR, a flame for the partial oxidation of the hydrocarbon is formed above a catalyst layer, and a produced gas by the partial oxidation is introduced to the catalyst layer, and then the reaction of the produced gas is carried out until reaching an equilibrium in the catalyst layer. It is considered that a space above the catalyst layer is enough if there is a height that the flame does not come into contact with the catalyst layer.

[Disclosure of the Invention]

[Problems to be Solved by the Invention]

A raw material effused from a burner to a furnace forms a flame in the burner, which is then diffused with a conical shape. An angle of breadth (a spreading angle) changes depending upon the shape of the burner, but is approximately 13 to 18°. A gas effused from a burner ordinarily exists in a turbulence region, but the spreading angle of this turbulent effusion flow does not change almost at all even when the pressure of the gas flow changes.

In a conventional ATR, since the effusion flow collides with the catalyst layer before diffusing to the inside wall of the furnace, a big circulating flow is generated, wherein a gas flowing in the lateral direction is ascends along the inside wall of the furnace, which then joins with the effusion flow from the burner, and then descends. That is, in a space above the catalyst layer of the conventional ATR, a gas sprayed to the catalyst layer flows outward on the catalyst layer, and a circulating flow, which is returned to the upper portion by colliding with the furnace wall, is formed.

If the circulating stream is generated, since the gas diffused from the burner descends with the big circulating stream, the gas sprayed from the burner takes a very short time to contact with the catalyst layer by passing only a portion of the space above the catalyst layer, not being secured a sufficient volume originally. Since the produced gas, which is not in a progressed state of the reaction, flows into the catalyst layer, the temperature of the upper portion of the catalyst layer is high.

Also, since the gas speed passing through the center of the catalyst layer becomes large in the catalyst layer, it is also impossible to perform an efficient reaction using uniformly the whole area of the catalyst layer.

The present inventors have found that a space above the catalyst layer contributes greatly to the reaction, and optimizing the space has been considered as an important means to solve the above problems.

[Means for Solving the Problems]

To solve the above problems, the present inventors have provided the catalyst layer at the downstream location of the point at which the effused flow from the burner reaches the inside wall of the furnace, and the flow at the furnace cross-section becomes completely downward.

That is, the invention described in the sixth embodiment of the present invention is that in a preparation furnace for preparing a synthesis gas which comprises effusing a raw material, which contains at least a hydrocarbon and an oxidizing agent, from a burner mounted at the top portion of the furnace; partially combusting the hydrocarbon in a space above a catalyst layer formed inside of the furnace; and preparing the synthesis gas containing hydrogen and carbon monoxide in the catalyst layer, the furnace is characterized in that it has a space to meet the conditions of the following (1) and (2), above the catalyst layer:

(1) $L \geq D/2 \times \cotan \theta_1$, and (2) A gas retention time in the space is 2 seconds or more wherein L is a height of the space above the catalyst layer, D is an inside diameter of the furnace, $\theta_1$ is a ½ angle of an apex angle in the vertical cross-section of a conical breadth of an effusion flow effused inside of the furnace from the burner, which is in the range of $6.5° \leq \theta_1 \leq 9°$.

The invention described in the seventh embodiment of the present invention is that in the furnace for preparing the synthesis gas described in the sixth embodiment of the present invention, the furnace is characterized by further fulfilling the condition of (3):

(3) $\theta_2 \geq 25°$ wherein $\theta_2$ is a ½ angle of an apex angle in the vertical cross-section of the top conical-shaped portion of the furnace.

The invention described in the eighth embodiment of the present invention is that in a furnace for preparing a synthesis gas containing hydrogen and carbon monoxide in a catalyst layer by effusing a raw material containing at least a hydrocarbon and an oxidizing agent from a burner mounted on the top portion of the furnace, and partially combusting the hydrocarbon in a space above the catalyst layer formed inside of the furnace, the furnace is characterized in that it has a space to meet the conditions of the following (1), (2) and (4), above the catalyst layer:

(1) $L \geq D/2 \times \cotan \theta_1$, (2) A gas retention time in the space is 2 seconds or more, and (4) $L \geq 10d$ wherein L is a height of the space above the catalyst layer, D is an inside diameter of the furnace, $\theta_1$ is a ½ angle of an apex angle in the vertical cross-section of a conical breadth of an effusion flow effused inside of the furnace from a burner, which is in the range of $6.5° \leq \theta_1 \leq 9°$, and d is a minimum diameter of a circle being capable of covering all the gas effusing holes of the burner.

The invention described in the ninth embodiment of the present invention is that in a furnace for preparing a synthesis gas containing hydrogen and carbon monoxide in a catalyst layer by effusing a raw material containing at least a hydrocarbon and an oxidizing agent from a burner mounted at the top portion of the furnace, and partially combusting the hydrocarbon in a space above a catalyst layer formed inside of the furnace, the furnace is characterized in that it has a space to meet the conditions of the following (1), (2), (3) and (5), above the catalyst layer:

(1) $L \geq D/2 \times \cotan q_1$, (2) A gas retention time in the space is 2 seconds or more, (3) $q_2 \geq 25°$, and (5) $D \geq 3d$ wherein L is a height of the space above the catalyst layer, D is an inside diameter of the furnace, $q_1$ is a ½ angle of an apex angle in the vertical cross-section of a conical breadth of an effusion flow effused inside of the furnace from the burner, which is in the range of $6.5° \leq \theta_1 \leq 9°$, $\theta_2$ is a ½ angle of an apex angle in the vertical cross-section of the top conical-shaped portion of the furnace, and d is a minimum diameter of a circle being capable of covering all the gas effusing holes of the burner.

The invention described in the tenth embodiment of the present invention is that in the furnace for preparing a synthesis gas described in the ninth embodiment of the present invention, the furnace is characterized by further fulfilling the condition of the following (4):

(4) $L \geq 10d$.

The invention described in the eleventh embodiment of the present invention is that in the furnace for preparing a synthesis gas according to any one of the sixth, seventh, eighth, ninth or tenth embodiments of the present invention, it is characterized in that the carbon dioxide concentration in the synthesis gas prepared by setting the outlet temperature of the catalyst layer at 1100 to 1300° C. is 10 vol % or less.

The invention described in the twelfth embodiment of the present invention is that in the furnace for preparing a synthesis gas described in the sixth embodiment of the present invention, it is characterized in that after terminating the catalytic reaction, the synthesis gas is rapidly cooled to 600° C. or less.

The invention described in the thirteenth embodiment of the present invention is that in the furnace for preparing a synthesis gas described in any one of the sixth, seventh, eighth, ninth, tenth, eleventh or twelfth embodiments of the present invention, it is characterized in that dimethyl ether is prepared from the synthesis gas containing carbon monoxide and hydrogen, which is prepared by the furnace for preparing the synthesis gas.

The invention described in the fourteenth embodiment of the present invention is that in the furnace for preparing a synthesis gas described in any one of the sixth, seventh, eighth, ninth, eleventh or twelfth embodiments of the present invention, it is characterized in that dimethyl ether is prepared from the synthesis gas containing carbon monoxide and hydrogen having the ratio of 1:0.8 to 1.2, which is prepared by the furnace for preparing the synthesis gas.

[Effects of the Invention]

In accordance with the present invention, it is possible to carry out a reaction in the absence of a catalyst effectively in a space above a catalyst layer, which is provided downstream of the location wherein a effused flow from a burner reaches the inside wall of a furnace, and the flow at the furnace cross-section becomes completely downward. For this reason, after sufficiently carrying out a reaction in the absence of the catalyst in the space above the catalyst layer, it is possible to further progress the reaction in the catalyst layer. Also, a uniform downward flow can be introduced in the catalyst layer, and thus it is possible to carry out an efficient reaction using uniformly the whole area of the catalyst layer.

[Best Mode for Carrying Out the Invention]

Hereinafter, an embodiment of the present invention will be described in detail.

Figure 2:
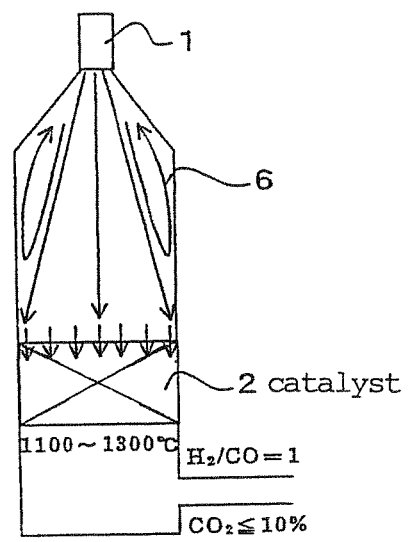
FIG. 2 is a vertical cross-sectional view of a furnace for preparing a synthesis gas in an embodiment of the present invention.

FIG. 2 shows an ATR as a furnace for preparing a synthesis gas in an embodiment of the present invention. In the ATR, a natural gas or a propane gas as a fuel; oxygen or air as an oxidizing agent; a steam as an auxiliary raw material; and carbon dioxide if necessary are effused from the burner 1 provided at the top portion of the furnace, to the inside of the furnace. And the natural gas is partially combusted in a space above the catalyst layer 2, and a gas produced by the partial combustion is reacted in the catalyst layer provided inside of the furnace up to an equilibrium, whereby the natural gas is reformed to a synthesis gas having hydrogen and carbon monoxide as main components.

The furnace for preparing the synthesis gas shown in FIG. 2 is characterized in that the whole shape is thin and long, as compared to a conventional flat furnace for preparing the synthesis gas shown in FIG. 7. This is to carry out efficiently the reaction in the absence of the catalyst in the space above the catalyst layer 2.

An effused flow from the burner 1 reaches the inside wall of the furnace, and the catalyst layer is provided downstream of the location where the flow at the furnace cross-section becomes completely downward, whereby it is possible for the effusion flow to carry out the reaction using effectively the volume inside the furnace. That is, as shown FIG. 3, if a height (L) of the space above the catalyst layer, which is given in the following formula, is secured with respect to an inside diameter D of the furnace, a good flow in the furnace can be formed even when the pressure or the gas flow rate is changed.

(1) $L \geq D/2 \times \cotan \theta_1$ wherein L is a height of the space above the catalyst layer, D is an inside diameter of the furnace, $\theta_1$ is a ½ angle of an apex angle in the vertical cross-section of a conical breadth of the effusion flow effused into the inside of the furnace from the burner, which is in the range of $6.5° \leq \theta_1 \leq 9°$.

Figure 3:
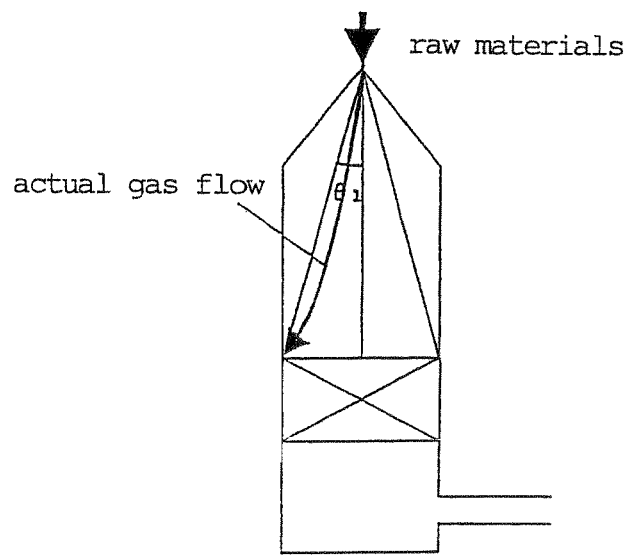
FIG. 3 is a vertical cross-sectional view of a furnace for preparing a synthesis gas (showing the definition of $\theta_1$)

When $\theta_1$ is further precisely described, as shown in FIG. 3, since a stream line is curved outward near the inside wall of the furnace, $\theta_1$ is a ½ angle of an apex angle of a conical shape formed by the apex portion of the effusion flow effusing into the inside of the furnace and the position of the inside wall of the furnace at which the effused flow reaches, by taking the vertical cross-section of the furnace in defining the conical breadth, which is in the range of $6.5° \leq \theta_1 \leq 9°$.

Figure 4:
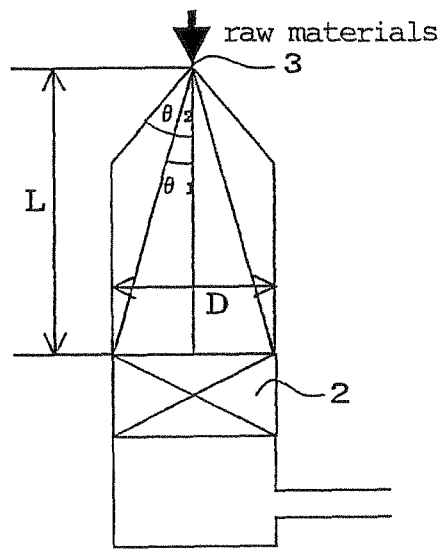
FIG. 4 is a vertical cross-sectional view of a furnace for preparing a synthesis gas.

In case wherein the diameter of the burner relative to the inside diameter D of the furnace is sufficiently small, as shown FIG. 4, the burner is considered as a point, and the raw material is diffused into a conical shape which has a ½ angle from a introducing point of the top portion of the furnace. In this case, the height L of the space above the catalyst layer is the distance from the apex 3 of the top portion of the furnace to the upper end of the catalyst layer 2.

Figure 5:
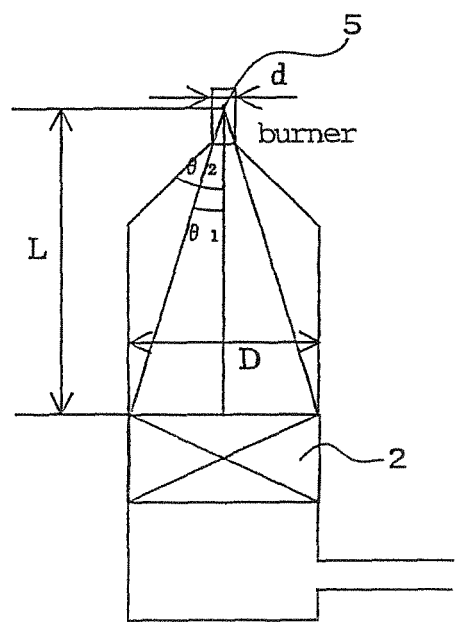
FIG. 5 is a vertical cross-sectional view of a furnace for preparing a synthesis gas.

On the other hand, in the case wherein the burner diameter is as big as to be compared with the inside diameter of the furnace D, the minimum diameter of the circle which can cover all the gas effusion holes of the burner is d, as shown in FIG. 5, it is considered that the raw material is diffused with a conical shape having an $\theta_1$ angle from the outside of the circle having the diameter of d.

In this case, the height L of the space above the catalyst layer is the distance from the apex 5 of a triangle of an apex angle ($2\theta_1$), which passes through the outside of a circle having the diameter of d, to the upper end of the catalyst layer 2 in the vertical cross-section of the top portion of the furnace.

A circulating flow 6 in the outside of the effusion flow shown in FIG. 2 is necessary for the protection of the furnace wall. Since the temperature of a flame formed in the burner is extremely high, in the case of directly spraying the flame to the furnace wall, the furnace wall can be melted. In order to separate the flame from the refractory material of the top portion of the furnace, it is necessary to circulate a gas, which has the temperature lowered after terminating the reaction, to the outside of the effusion flow. For the circulating flow formed around the top portion of the furnace, if the apex angle at the top portion of the furnace which has a conical form is 50° or more, preferably 60° or more, the circulating flow has a sufficient strength, and it is possible that the temperature of the inside wall of the furnace at the top portion thereof can be set at the temperature below an ordinary heat-resistant temperature. In this case, the circulating flow does not reach the catalyst layer. For this reason, as shown in FIG. 4 and FIG. 5, $\theta_2$, which is a ½ angle of an apex angle in the vertical cross-section of the top portion of the furnace, which has a conical shape, is set to $\theta_2 \geq 25°$.

In case wherein the flow from the burner is assumed to be effused from a big single hole, a potential core exists in the center of the effusion flow. The potential core is a region which maintains a uniform gas effusing speed, not mixing with the surrounding flow. In order for the potential core to disappear and for the effusion flow to mix uniformly, it is necessary to secure an effusion distance of 10 times or more with respect to the diameter of the single hole. In practice, there are many cases of effusing out of a plurality of holes from the burner, but if the height of a space above the catalyst layer having the following height using d is secured, the potential core disappears in any burners, and it is possible to introduce a uniformly mixed gas to the catalyst layer.

(4) $L \geq 10d$

Also, if a minimum diameter of a circle is d, which can cover all the gas effusion holes of the burner, in case where d is big as compared to the inside diameter D of the furnace, a space being capable of forming a sufficient circulating flow can not be secured. The condition for forming the sufficient circulating flow is as follows:

(5) $D \geq 3d$

From the above description, a furnace shape can be obtained, but a method for defining the size thereof is described as follows.

As for an ATR running under various conditions, a gas at various heights of the space above the catalyst layer is rapidly cooled and collected, and is analyzed. The inventors have found that a necessary retention time for nearly completing the reaction in the absence of a catalyst is 2 seconds or more, preferably 3 seconds or more. Based on this, (2) the retention time of a gas in the space is set at 2 seconds or more. The term "retention time" means a passing time of a produced gas through the volume of the space above the catalyst layer, calculated by converting the temperature and pressure of the gas to those in the space.

By securing the retention time, the concentration of a hydrocarbon contained in a gas, which reaches the catalyst layer, can be lowered. Since the decomposition of a hydrocarbon is a strong endothermic reaction, reducing the concentration of the hydrocarbon lowers efficiently the temperature of the gas flowing into the catalyst layer, thereby lengthening the life span of the catalyst. In a conventional ATR, since the concentration of the hydrocarbon is not lowered sufficiently, as to 900 to 1050° C. of the outlet temperature of the catalyst, the inlet temperature of the catalyst is raised up to about 1400° C., which is a limiting heat-resistant temperature of an ordinary Ni-based catalyst. For this reason, as a heat shield, a catalyst having a high heat-resistance is provided at the top portion of the catalyst layer. That is, a large reduction of the temperature occurs inside of the catalyst layer. Contrary to this, by reducing the concentration of the hydrocarbon in the inlet of the catalyst layer to a half or less, it is possible to reduce the decrease in the temperature in the inside of the catalyst layer to a half or less of the above case. Also, in case where the temperature of the inlet of the catalyst layer is set at 1350° C., it is possible that the outlet temperature of the catalyst layer is 1100 to 1300° C., as described below.

Also, lowering the concentration of the hydrocarbon contained in the gas reaching the catalyst, the necessary amount of the catalyst can be reduced.

The above description relates to a method for optimizing the space above the catalyst layer. Also, in order to solve the above problems, the present inventors have investigated in view of an equilibrium temperature. As a result, the following knowledge has been obtained.

The concentration of a hydrocarbon contained in a gas reaching a catalyst layer is lowered to protect the catalyst, and the outlet temperature of the catalyst layer reaching an equilibrium is set at 1100 to 1300° C., whereby soot is not formed although the ratio of hydrogen to carbon monoxide is lowered, and also the amount of carbon dioxide as an auxiliary raw material can be lowered. As a result, it is possible that the carbon dioxide concentration in a produced gas is 10 vol % or less using a natural gas fuel, and the carbon dioxide concentration in the produced gas is 5 vol % or less using a propane gas fuel. Also, since the catalyst is operated efficiently at high temperatures, a high price catalyst containing a noble metal is not necessary, and also the amount of the catalyst may be decreased.

After terminating the catalytic reaction, it is preferable that the synthesis gas is rapidly cooled to 600° C. or less. In this way, thereafter, the gas composition may not be changed, and a gas having the gas composition at the outlet of the catalyst layer can be delivered to the downstream synthetic reaction.

The reformed synthesis gas is used as a raw material for the synthesis of dimethyl ether (DME), F-T, methanol, ammonia, and so on. Hereinafter, a method for synthesizing dimethyl ether (DME) will be described schematically, wherein the synthesis gas having carbon monoxide and hydrogen as main components is passed and reacted through a slurry reactor in which a catalyst in fine particles is suspended in a high-boiling point medium oil.

A method for synthesizing dimethyl ether from carbon monoxide and hydrogen is carried out, simultaneously performing the three reactions of the synthesis of methanol produced from hydrogen and carbon monoxide, the synthesis of dimethyl ether produced by a dehydration reaction of the above synthesized methanol, and the production of hydrogen by the reaction of carbon monoxide and water by-produced accompanied with the above dimethyl ether synthesis, which are represented by the following formulae (A), (B) and (C).

$$CO + 2H_2 \rightarrow CH_3OH \quad (A)$$

$$2CH_3OH \rightarrow CH_3OCH_3 + H_2O \quad (B)$$

$$H_2O + CO \rightarrow H_2 + CO_2 \quad (C)$$

The summarization of (A) to (C) is shown as the formula (D) below. Dimethyl ether and carbon dioxide are produced in equal amounts from hydrogen and carbon monoxide.

$$3CO + 3H_2 \rightarrow CH_3OCH_3 + CO_2 \quad (D)$$

In order to use as a raw material of this reaction, in case of lowering the ratio of hydrogen to carbon monoxide in a synthesis gas to 2 or less, the increase of the carbon dioxide concentration in a produced synthesis gas and the occurrence of soot is not negligible. In the synthesis process of dimethyl ether using the formula (D), a synthesis gas having 1:1 of the ratio of hydrogen to carbon monoxide is necessary, but in an ordinary ATR, the carbon dioxide concentration in the produced synthesis gas reaches 20 to 40 vol % on the dry basis.

Carbon dioxide contained in a raw gas inhibits the reaction, thereby it adversely affects the manufacturing process. Also, the circulation of a large amount of carbon dioxide in the reaction system is not desired for the apparatus cost and the operating cost.

In order to prevent these disadvantages, a process for removing $CO_2$ from a raw gas may be additionally conceived, but it would result in increase in the apparatus cost and the operating cost.

As described above, the temperature reaching an equilibrium is set at 1100 to 1300° C., and the ratio of hydrogen to carbon monoxide (molar ratio) is lowered to nearly 1, and also the carbon dioxide concentration is lowered, whereby it becomes effective in the dimethyl ether synthesis represented by the overall reaction formula (D).

In addition, the kind of the catalyst used in this embodiment is not particularly limited if a heat resistance is satisfied at the reaction temperature of 1100 to 1300° C. Examples of the catalyst include a metal such as titanium, vanadium, chromium, manganese, iron, cobalt, nickel, copper, zinc, potassium, yttrium, zirconium, niobium, molybdenum, ruthenium, rhodium, palladium, gold, cadmium, indium, tin, hafnium, tantalum, tungsten, rhenium, osmium, iridium, platinum, silver, mercury, tellurium, lead, bismuth, thallium, uranium, lithium, sodium, potassium, rubidium, cesium, beryllium, magnesium, calcium, strontium, barium, boron, aluminum, scandium, thorium, lead and lanthanoid, an oxide thereof, and the like.

The catalyst can be supported on a carrier. The carrier can be used singly or in a combination of two or more selected from the group consisting of alumina, silica, titania, zirconia, magnesia, zeolite, etc.

The particle size and shape of the catalyst is not particularly limited, but a large surface area and a small pressure drop are preferable.

Also, as a fuel introduced to an ATR, a natural gas including a large amount of $N_2$ and $CO_2$, a coal bed methane, an associated gas, an organic fermentation methane, a gas for manufacturing iron, etc., in addition to a natural gas and an LPG gas, can be used. As an oxidizing agent introduced in the ATR, a pure $O_2$, air and an $O_2$ enriched air can be used.

The pressure is in the range of atmospheric pressure to 50 atm, but is not particularly limited.

EXAMPLES

Figure 6:
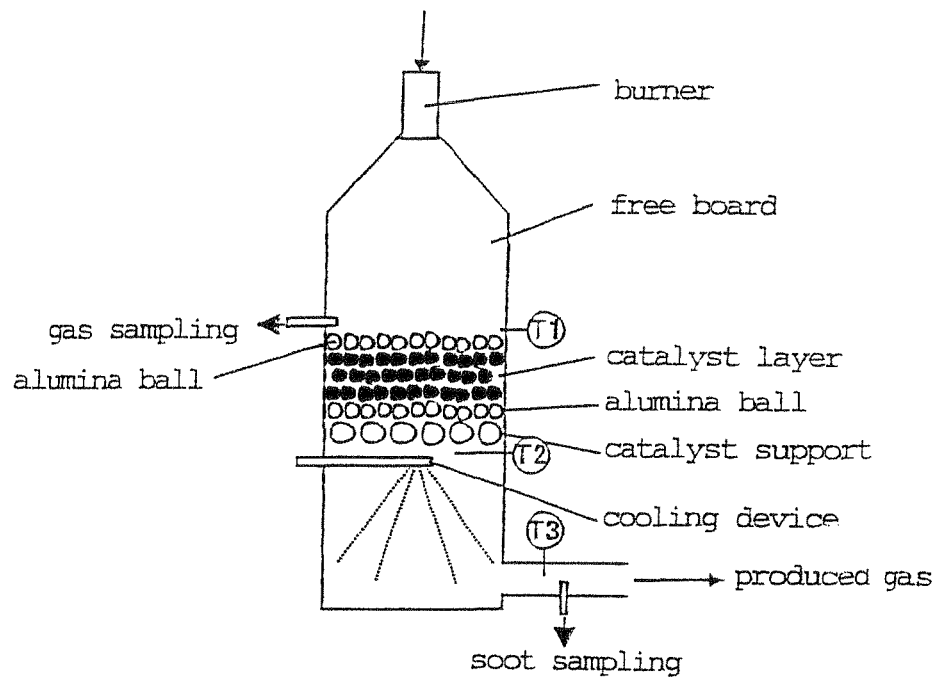
FIG. 6 is a vertical cross-sectional view of a furnace for preparing a synthesis gas.

A hydrocarbon gas was reformed to carbon monoxide gas and hydrogen gas by using a furnace for preparing a synthesis gas as shown in FIG. 6. In the upper portion and lower portion of a catalyst layer, alumina balls were placed as an adiabatic layer. The catalyst layer was supported by a catalyst carrier. In the downstream of the catalyst layer, a cooling means for cooling the synthesis gas by spraying water was provided.

The inside pressure of the furnace was set to 0.6 MPa. The retention time of a freeboard portion was calculated from the volume of the freeboard portion, the flow rate of a produced gas (the wet flow rate), and the temperature and pressure of the freeboard portion.

In Examples 1 to 3, the outlet temperature of the catalyst layer was set at 1100 to 1300° C., and the retention time in the freeboard portion, which was a space above the catalyst layer, was set to 2 seconds or more. Also, the ratio of hydrogen to carbon monoxide in the synthesis gas obtained by rapid-cooling of the synthesis gas to 600° C. or less in the lower portion of the catalyst layer, was set to 0.8 to 1.2.

In Comparative Example 1, it was performed under the condition that the outlet temperature T2 of the catalyst layer was lowered to 960° C.

In Comparative Example 2, the aluminum ball layer under the catalyst layer was made thick, and the freeboard portion was made small. As for the inlet temperature T1 of the catalyst layer, the temperature immediately above the top of the packed bed, which was increased in the height, was measured.

A composition of the raw gas, the volume of the freeboard portion, the retention time in the freeboard portion, the inlet temperature of the catalyst layer, the concentration of $CH_4$ in the inlet of the catalyst layer, the outlet temperature of the catalyst layer, the temperature after rapid-cooling, the composition of the produced gas, the concentration of soot with regard to Examples 1 to 3 and Comparative Examples 1 and 2, are indicated in Table 1 below.

TABLE 1

|  |  |  | Example | | | | Comparative Example | |
| --- | --- | --- | --- | --- | --- | --- | --- | --- |
|  |  |  | 1 | 2 | 3 | 4 | 1 | 2 |
| Raw gas | Natural gas | [Nm³/h] | 400 | 400 | 400 | 0 | 400 | 400 |
|  | Propane gas | [Nm³/h] | 0 | 0 | 0 | 180 | 0 | 0 |
|  | $O_2$ | [Nm³/h] | 352 | 342 | 328 | 315 | 338 | 342 |
|  | $CO_2$ | [Nm³/h] | 196 | 214 | 210 | 101 | 401 | 216 |
|  | $H_2O$ | [Nm³/h] | 34 | 21 | 0 | 24 | 200 | 24 |
| Volume of freeboard portion |  | [m³] | 0.90 | 0.90 | 0.90 | 0.90 | 0.90 | 0.20 |
| Retention time of freeboard portion |  | [s] | 2.17 | 2.29 | 2.49 | 2.55 | 2.23 | 0.50 |
| Inlet temp. of catalyst layer T1 |  | [° C.] | 1302 | 1280 | 1249 | — | 1238 | 1392 |
| Concentration of $CH_4$ in the inlet of catalyst layer |  | [dry vol %] | 0.2 | 1.7 | 3.1 | — | 8.5 | 4.6 |
| Outlet temp. of catalyst layer T2 |  | [° C.] | 1290 | 1200 | 1105 | 1230 | 960 | 1200 |
| Temp. after rapid-cooling T3 |  | [° C.] | 550 | — | 500 | 480 | 500 | 500 |
| Composition of Produced gas | CO | [dry vol %] | 45.3 | 45.1 | 44.2 | 47.7 | 38.9 | 45.0 |
|  | $CO_2$ | [dry vol %] | 9.3 | 9.8 | 9.3 | 4.6 | 21.8 | 9.9 |
|  | $H_2$ | [dry vol %] | 45.3 | 45.1 | 46.5 | 47.7 | 38.9 | 45.0 |
|  | $CH_4$ | [dry vol %] | 0.0 | 0.0 | 0.0 | 0.0 | 0.4 | 0.0 |
| Concentration of soot |  | [g/Nm³] | 0.00 | 0.00 | 0.00 | — | 0.17 | 0.08 |

As confirmed in Examples 1 to 3, the concentration of $CH_4$ in the inlet of the catalyst layer was lowered to less than 3.5 vol %, whereby the difference between the inlet temperature of the catalyst and the outlet temperature thereof became small. Also, the carbon dioxide concentration in the synthesis gas was 10 vol % or less in case of introducing a natural gas as a fuel, and was lowered to 5 vol % in case of introducing a propane gas. In Example 2, the temperature after the rapid-cooling was changed to 595 to 350° C., but the change of the produced gas composition (dry composition) did not occur.

In Comparative Example 1, due to the remaining $CH_4$, the inlet temperature T1 of the catalyst layer was not lowered as much as the outlet temperature, and also the carbon dioxide concentration in the synthesis gas was in excess of 20 vol %.

In Comparative Example 2, the concentration of methane in the inlet of a catalyst layer was increased as compared to Example 2. Also, the outlet temperature of the catalyst layer in all of Comparative Example 2 and Example 2 was 1200° C., while the inlet temperature of the catalyst layer in Comparative Example 2 was increased by about 100° C. than Example 2.

<As for a Third Invention>

Fifteenth Embodiment of the Present Invention

A method for preparing a synthesis gas containing carbon monoxide and hydrogen in the presence of a catalyst by using a fuel gas and an oxidizing agent as raw materials, wherein a portion of the prepared synthesis gas is fed as a portion of raw materials at the time of preparing the synthesis gas.

Sixteenth Embodiment of the Present Invention

A method for preparing a synthesis gas containing carbon monoxide and hydrogen in the presence of a catalyst by using a fuel gas and an oxidizing agent as raw materials, wherein a portion of the gas of the following (a) and/or (b) is fed as a portion of raw materials at the time of preparing the synthesis gas:

(a) an outlet gas containing carbon monoxide and hydrogen discharged from a reaction system in a process using the prepared synthesis gas as a raw material;

(b) a gas containing carbon monoxide and hydrogen separated from a product in a post-process, accompanying with an obtained product in a process using the prepared synthesis gas as a raw material.

Seventeenth Embodiment of the Present Invention

The method for preparing a synthesis gas according to the fifteenth embodiment of the present invention, wherein a portion of the prepared synthesis gas is mixed with a fuel gas, which is then fed as a portion of raw materials at the time of preparing the synthesis gas.

Eighteenth Embodiment of the Present Invention

The method for preparing a synthesis gas according to the sixteenth embodiment of the present invention, wherein a portion of a gas of (a) and/or (b) is/are mixed with the fuel gas, which is then fed as a portion of raw materials at the time of preparing the Nineteenth Embodiment of the Present Invention A furnace for preparing a synthesis gas containing carbon monoxide and hydrogen in the presence of a catalyst by using a fuel gas and an oxidizing agent as raw materials, which is provided with a synthesis gas feed line which feeds a portion of the prepared synthesis gas as a portion of raw materials at the time of preparing the synthesis gas.

[Technical Field]

The present invention relates to a method for preparing a synthesis gas from a gas containing a hydrocarbon, carbon dioxide, oxygen, etc. Also, the synthesis gas is suitable one as a synthesis gas having the ratio of $H_2/CO=0.8$ to 1.2 (molar ratio), which is required for synthesizing dimethyl ether (DME).

[Background Art]

A synthesis gas containing hydrogen and carbon monoxide is used as raw materials for the synthesis of F-T, methanol, ammonia, DME, etc.

The synthesis gas is prepared from various organic compounds. As a method for preparing the synthesis gas, a method such as a reaction of steam and/or carbon dioxide, a partial oxidation by oxygen and/or air, etc. are known.

Especially, for a gaseous organic compound, the following methods are used: (1) a method for reacting steam and/or carbon dioxide to an organic compound in the presence of a catalyst at high temperatures; (2) a method comprising a partial oxidization of an organic compound by using oxygen and/or air to generate a heat, with which steam and/or carbon dioxide is mixed, which is then reacted in a catalyst layer; or (3) a combination of (1) and (2).

[Disclosure of the Invention]

[Problems to be Solved by the Invention]

However, in the process for preparing a synthesis gas accompanying with a partial oxidation, the temperature of the top portion of a furnace used at the time of preparing the synthesis gas is raised. For this reason, there are problems on the plant, such as the melting of refractory materials in the furnace, etc.

Therefore, under the above circumstances, the present invention has an object to provide a method for preparing a synthesis gas, which lowers the temperature of the top portion of the furnace used at the time of preparing the synthesis gas.

The present inventors have studied intensively to solve the above problems. As a result, it was found that the temperature of the top portion of a furnace used at the time of preparing a synthesis gas is lowered by feeding a portion of the synthesis gas containing carbon monoxide and hydrogen, which is prepared by a process of preparing the synthesis gas; a portion of an outlet gas containing carbon monoxide and hydrogen discharged from a reaction system in a process of using a produced synthesis gas as a raw material; or a portion of a gas containing carbon monoxide and hydrogen separated from a product in the post-process, accompanying with an obtained product in a process of using the produced synthesis gas as a raw material, preferably feeding the above gas mixed with a fuel gas.

The present invention has been accomplished on the basis of the finding as described above. The present invention is characterized in that:

The invention described in the twentieth embodiment of the present invention is a method for preparing a synthesis gas containing carbon monoxide and hydrogen in the presence of a catalyst by using a fuel gas and an oxidizing agent as raw materials, wherein a portion of the prepared synthesis gas is fed as a portion of raw materials at the time of preparing the synthesis gas.

The invention described in the twenty-first embodiment of the present invention is a method for preparing a synthesis gas containing carbon monoxide and hydrogen in the presence of a catalyst by using a fuel gas and an oxidizing agent as raw materials, wherein a portion of the gas of the following (a) and/or (b) is fed as a portion of raw materials at the time of preparing the synthesis gas:

(a) an outlet gas containing carbon monoxide and hydrogen discharged from a reaction system in a process using, the prepared synthesis gas as a raw material;

(b) a gas containing carbon monoxide and hydrogen separated from a product in a post-process, accompanying with an obtained product in a process using the prepared synthesis gas as a raw material.

The invention described in the twenty-second embodiment of the present invention is the method for preparing a synthesis gas according to the twentieth embodiment of the present invention, wherein a portion of the prepared synthesis gas is mixed with a fuel gas, which is then fed as a portion of raw materials at the time of preparing the synthesis gas.

The invention described in the twenty-third embodiment of the present invention is the method for preparing a synthesis gas according to the twenty-first embodiment of the present invention, wherein a portion of a gas of (a) and/or (b) is/are mixed with the fuel gas, which is then fed as a portion of raw materials at the time of preparing the synthesis gas.

The invention described in the twenty-fourth embodiment of the present invention is a furnace for preparing a synthesis gas containing carbon monoxide and hydrogen in the presence of a catalyst by using a fuel gas and an oxidizing agent as raw materials, which is provided with a synthesis gas feed line which feeds a portion of the prepared synthesis gas as a portion of raw materials at the time of preparing the synthesis gas.

[Effects of the Invention]

In the present invention, it is possible to lower the temperature of the top portion of a furnace used at the time of preparing a synthesis gas. And since the temperature of the top portion of the furnace is lowered, it is not required to give heat-resistance to the top portion of the preparation furnace; the frequency to repair the refractory materials is decreased; or the like, thus time and cost for the plant maintenance are not required. Therefore, the present invention is economical. Also, the amount of carbon dioxide in the prepared synthesis gas may be efficiently decreased without increasing the outlet temperature of a catalyst layer of the furnace by returning the synthesis gas containing carbon monoxide and hydrogen as raw materials.

[Best Mode for Carrying Out the Invention]

Hereinafter, the present invention will be described in detail.

Figure 8:
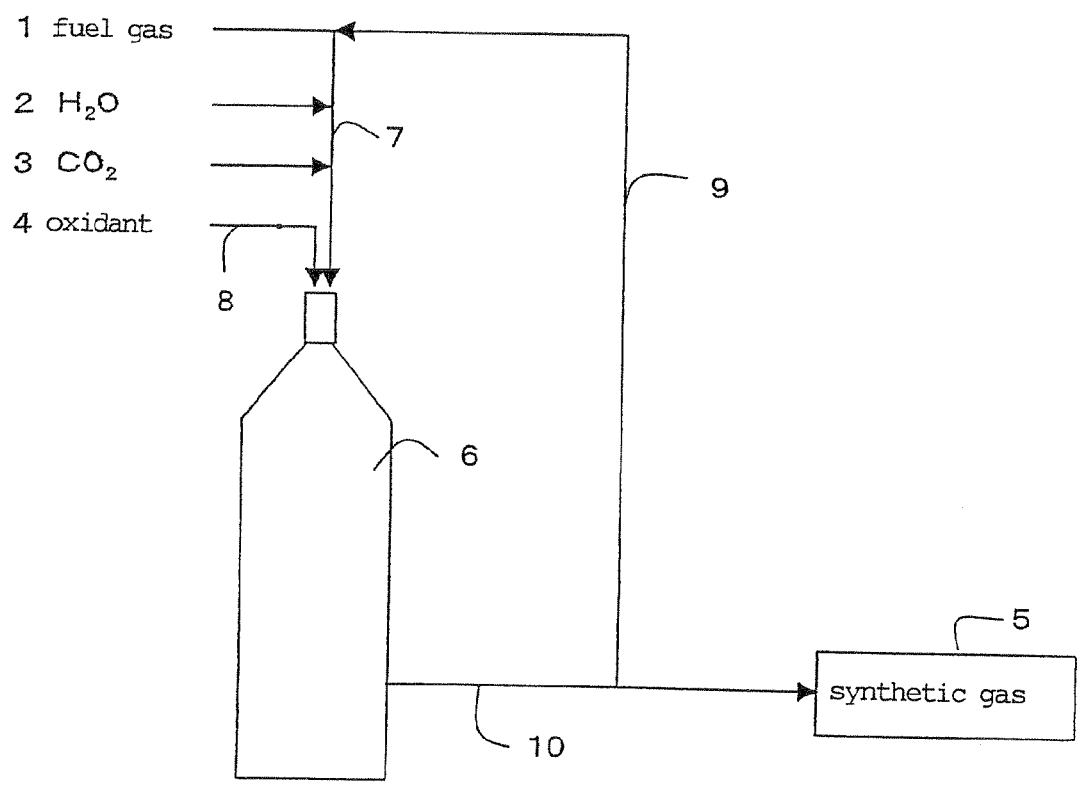
FIG. 8 is a schematic diagram showing a furnace for preparing a synthesis gas according to an embodiment of the present invention.

FIG. 8 is a schematic diagram showing an embodiment of a furnace for preparing a synthesis gas (an auto-thermal reformer (ATR)) according to the present invention. In preparing a synthesis gas (5) containing carbon monoxide and hydrogen, gas as a raw material is classified into a fuel gas (1), an oxidizing agent (4) and auxiliary raw materials (2) and (3). The fuel gas (1) is a hydrocarbon comprising a natural gas, an LPG, hydrocarbons (HC) or the like. The oxidizing agent (4) includes oxygen, air or the like. Also, the auxiliary raw material includes steam (water) (2), carbon dioxide (3) or the like.

A catalyst layer is provided inside of a furnace for preparing the synthesis gas (hereinafter, referred to as a preparation furnace in short) (6). The synthesis gas containing carbon monoxide and hydrogen, for example, the gas produced by partial oxidation using a diffusion mixing type burner, is prepared from the above-described raw gas in the presence of a catalyst. That is, by means of the furnace for preparing the synthesis gas, the synthesis gas having hydrogen and carbon monoxide as main components is prepared by catalytically reforming the gas generated by the partial combustion of the hydrocarbon.

In FIG. 8, (1) is the fuel gas, (4) is the oxidizing agent, (5) is the synthesis gas, and (6) is the preparation furnace. To the fuel gas feed line (7) for feeding the fuel gas (1) to the preparation furnace (6), a feed line for feeding auxiliary raw materials of steam (2) and carbon dioxide (3) is connected. Further, prior to introducing them to the preparation furnace (6), steam (2) and carbon dioxide (3) are premixed with the fuel gas (1).

An oxidizing agent feed line (8) for feeding an oxidizing agent (4) to the preparation furnace (6) is not connected to the fuel gas feed line (7), but is connected directly to the preparation furnace (6). The reason is that if the oxidizing agent (4) is premixed with the fuel gas, the fuel gas (1) is burned. It is effective to inhibit the soot production or the partial increase of the inside temperature of the furnace by preliminarily introducing the raw materials other than the oxidizing agent, namely, steam (2) and carbon dioxide (3) into the preparation furnace (6), which are then mixed with the oxidizing agent (4) in the preparation furnace (6).

A synthesis gas feed line (9) for circulating the prepared synthesis gas (5) in the preparation furnace (6) is branched from a synthesis gas drain line (10), and is connected to the fuel gas feed line (7). Thus, a portion of the prepared synthesis gas (5) is fed to the preparation furnace (6) as a portion of the raw gas at the time of preparing the synthesis gas. Also, it is preferable that after premixing the circulated synthesis gas with the fuel gas (1), carbon dioxide (3) and steam (2), the mixture is fed to the preparation furnace, and the synthesis gas circulated in the furnace is reacted with oxygen. But, the feeding method is not limited thereto.

In a conventional furnace for preparing the synthesis gas, the temperature of the top portion of the furnace is increased, such that refractory materials in the furnace are melted. Therefore, there are problems in the plant. First, this will be described as follows.

As described above, in preparing a synthesis gas containing carbon monoxide and hydrogen, a raw gas is classified into a fuel gas and an oxidizing agent, or further an auxiliary raw material. The synthesis gas containing carbon monoxide and hydrogen, for example, the gas produced by partially oxidation using a diffusion mixing-type burner, is prepared from the above-described raw gas in the presence of a catalyst. At this time, if a high concentration of oxygen is combined with a high concentration of the fuel gas in the reaction, more heat is generated, whereby the top portion of the furnace is heated up, so that the temperature thereof is increased.

It was found that that it is possible to lower the flame temperature by returning and feeding a portion of the synthesis gas containing carbon monoxide and hydrogen, as a portion of the raw materials, obtained at the time of preparing the synthesis gas, thus lowering the highest temperature of the top portion of the preparation furnace. The oxidizing agent is reacted with circulated hydrogen ($H_2$) and carbon monoxide (CO), in addition to the fuel gas. Since heat generated by the oxidation of $H_2$ and CO is small compared to that of the fuel gas, the temperature of the region with high concentration of the oxidizing agent, is effectively lowered. $H_2O$ and $CO_2$ produced by the oxidation of $H_2$ and CO are the oxidizing agents of the unreacted fuel gas in the subsequent region, and they are reduced to $H_2$ and CO. That is, $H_2$ and CO are a medium for oxygen exchange, and since not all of $H_2$ and CO are reacted, thus increasing the gas volume, the highest temperature of the top portion of the furnace is lowered. Here, the peak temperature of the flame is lowered by decreasing the concentration of the fuel gas, and simultaneously, it is possible to lower the temperature of all the regions of the furnace by adding the unreacted gas, which is eventually not related to the combustion (that is, the synthesis gas containing carbon monoxide and hydrogen). The added $H_2$ and CO act as an inert gas in the furnace. Also, contrary to the case of adding the inert gas such as $N_2$ etc, the added $H_2$ and CO do not increase the impurities in the produced gas, and the concentrations of $H_2$ and CO which are the useful components in the produced gas, are not decreased, but increased.

The produced synthesis gas contains carbon monoxide, carbon dioxide, hydrogen and water (steam), which maintain an equilibrium by the shift reaction as shown in the following reaction formula (1).

$$CO+H_2O=CO_2+H_2 \quad (1)$$

The amounts of the introduced hydrocarbon, oxygen, carbon dioxide and steam are maintained, and if hydrogen and carbon monoxide having the same ratio of hydrogen/carbon monoxide as the produced gas are introduced in the preparation furnace, the inside temperature of the furnace (from the top portion of the furnace to the outlet of the catalyst layer) can be lowered while nearly maintaining the composition of the produced gas. This is because the introduced hydrogen and carbon monoxide are not changed eventually, and have an effect to dilute the gas in the furnace. Also, since the denominator and the numerator of the shift equilibrium shown as $([CO] \times [H_2O])/([CO_2] \times [H_2])$ of the produced gas are increased with the same proportion, the equilibrium is almost not shifted. This is an effective means for protecting the refractory materials in the furnace because the similar gas composition can be obtained at lower temperatures.

Furthermore, if the inside temperature of the preparation furnace is raised, the amount of carbon dioxide in the prepared synthesis gas can be lowered. But the amount of carbon dioxide in the prepared synthesis gas can be effectively lowered without raising the temperature in the furnace by returning the synthesis gas containing carbon monoxide and hydrogen as the raw gas. Hereinafter, the effect will be described in detail.

For example, in a process for synthesizing dimethyl ether from a synthesis gas containing carbon monoxide and hydrogen as shown in the following formula (2), the synthesis gas having the ratio of 1:1 of hydrogen to carbon monoxide is needed:

$$3H_2+3CO \rightarrow CH_3OCH_3+CO_2 \quad (2).$$

However, in the case of preparing the synthesis gas (a mixed gas having hydrogen and monoxide as main components) by using a natural gas or a propane gas as a raw material, the molar ratio of hydrogen/carbon monoxide is generally 2 or more. Therefore, in the case of using the synthesis gas in the process for synthesizing dimethyl ether, the molar ratio of hydrogen/carbon monoxide in the synthesis gas should be decreased. In order to decrease the ratio Of hydrogen in the synthesis gas, for example, carbon dioxide is introduced in the process for preparing the synthesis gas, and is then reacted with hydrogen as shown in the following formula (3), thus effectively increasing carbon monoxide:

$$H_2+CO_2 \rightarrow CO+H_2O \quad (3).$$

However, since the formula (3) is an equilibrium reaction, not all of the introduced carbon dioxide is reacted, such that the unreacted carbon dioxide, that is the excess carbon dioxide, remains in the produced synthesis gas. In practice, in order to obtain the ratio of 1:1 of hydrogen to carbon monoxide, carbon dioxide is generally added at more than the flow rate of the raw gas such as a natural gas, etc., thus the concentration of carbon dioxide contained in the prepared synthesis gas, reaches up to 20 to 40% on the dry basis.

The produced synthesis gas comprises carbon monoxide, carbon dioxide, hydrogen and water (steam), which maintain the equilibrium by the shift reaction as shown in the following reaction formula (1), as described above.

$$CO + H_2O = CO_2 + H_2 \tag{1}$$

In order to increase carbon monoxide (CO) and decrease hydrogen ($H_2$), it is possible to shift the reaction to the left side of the equation by adding carbon dioxide ($CO_2$) to the system. However, this increases the carbon dioxide concentration in the synthesis gas, as described above. On the other hand, at higher temperatures, the reaction shifts more the left side of the equation, while at lower temperatures, the reaction shifts more to the right side of the equation. Thus, in order to decrease hydrogen, namely, to increase carbon monoxide the reaction should be carried out at higher temperatures. By increasing the temperature, carbon dioxide added to the system is decreased. It is possible to realize a low ratio of $H_2/CO$ by maintaining the concentration of $CO_2$ contained in the synthesis gas at a low level. That is, as the outlet temperature of the catalyst layer is raised, the $CO_2$ concentration of the synthesis gas can be lowered.

As described above, in order to decrease the concentration of $CO_2$ contained in the produced gas, it is preferable that the outlet temperature of the catalyst layer is high. However, on the other hand, although it is possible to decrease the $CO_2$ concentration by raising the outlet temperature of the catalyst layer, the energy efficiency is lowered. Further, since the heat load to the furnace body is increased, an expensive material is required, or the life of the furnace body is decreased. Accordingly, in the present embodiment, in order to decrease the $CO_2$ concentration to 10% or less, the outlet temperature of the catalyst layer is set at 1100 to 1300° C.

The present inventors have investigated a method for further decreasing the concentration of $CO_2$ contained in the synthesis gas. As a result, the followings have been found.

Carbon dioxide and steam as the auxiliary raw materials can lower the temperature of the produced gas, and also they are introduced to control the composition of the produced gas. As described above, if hydrogen and carbon monoxide in the prepared synthesis gas are introduced into the preparation furnace, the outlet temperature of the catalyst layer in the preparation furnace is lowered. If carbon dioxide and steam that are the raw gas is decreased so as to maintain the outlet temperature of the catalyst layer, the $CO_2$ and $H_2O$ concentrations in the produced gas can be lowered. Although carbon dioxide and steam in the raw gas are involved in the reaction, most of them exist in the produced gas. Therefore, the $CO_2$ and $H_2O$ concentrations in the produced gas can be lowered in proportion to the decreased amount of carbon dioxide and steam that are the raw gas. The process for decreasing carbon dioxide and steam of the raw gas is regulated by calculating the equilibrium, whereby a predetermined ratio of $H_2/CO$ can be maintained. That as described above, it is possible to further decrease the $CO_2$ concentration in the produced gas that is already lowered by raising the outlet temperature of the catalyst layer.

In the case of introducing hydrogen and carbon monoxide for the purpose of lowering the $CO_2$ concentration, when the synthesis gas contains $CO_2$ and $H_2O$, each of the amounts of $CO_2$ and $H_2O$ should be decreased from the amounts of $CO_2$ and steam which are individually introduced as the auxiliary raw materials. This means that, after decreasing the amounts of $CO_2$ and $H_2O$ corresponding to the amounts for maintaining the outlet temperature of the catalyst layer with respect to the introduced hydrogen and carbon monoxide, each of the amounts of $CO_2$ and $H_2O$ contained in the synthesis gas is further decreased.

As described above, the present invention is characterized in that, in order to lower the temperature of the top portion of the furnace and further to decrease the amount of $CO_2$ contained in the synthesis gas, a portion of the synthesis gas containing carbon monoxide and hydrogen, which is obtained as the produced gas at the time of preparing the synthesis gas, is returned and fed as a portion of the raw material at the time of preparing the synthesis gas.

As a method for introducing hydrogen and carbon monoxide, a method of circulating a portion of the prepared synthesis gas in the synthesis gas preparation furnace and a method of feeding an outlet gas containing carbon monoxide and hydrogen discharged from the reaction system in the process using the prepared synthesis gas as the raw material are suitably used.

The same effect as the above method was obtained in the case of using a portion of a gas containing carbon monoxide and hydrogen, which was separated from the product in a post-process, accompanying with the product obtained in the process using the prepared synthesis gas as a raw material.

In the condition for the preparation of the synthesis gas having the $H_2/CO$ ratio of 1, the amount of the introduced steam is small. Therefore, there is a limitation in decreasing the amount. In most of the cases of using an outlet gas containing carbon monoxide and hydrogen, which is discharged from the reaction system in the process using the synthesis gas as the raw material, $H_2O$ is not contained, and therefore it is not necessary to decrease the amount of steam corresponding to the amount of $H_2O$. However, in the case of circulating the synthesis gas at temperatures higher than the water vapor condensation temperature, there is a problem. In such case, it is preferable to reduce the temperature of the synthesis gas to the vapor condensation temperature or lower to remove the water vapor, and then to introduce the synthesis gas to the preparation furnace.

As described above, the preparation of the synthesis gas according to the present invention, is accomplished by using a fuel gas, an oxidizing agent or further an auxiliary raw material as raw materials in the presence of a catalyst. The kind of the catalyst is not particularly limited, if a heat resistance is satisfied at the reaction temperature (for example, 1100 to 1300° C.). Examples of the catalyst include a metal such as titanium, vanadium, chromium, manganese, iron, cobalt, nickel, copper, zinc, potassium, yttrium, zirconium, niobium, molybdenum, ruthenium, rhodium, palladium, gold, cadmium, indium, tin, hafnium, tantalum, tungsten, rhenium, osmium, iridium, platinum, silver, mercury, tellurium, lead, bismuth, thallium, uranium, lithium, sodium, potassium, rubidium, cesium, beryllium, magnesium, calcium, strontium, barium, boron, aluminum, scandium, thorium, lead, lanthanoid, etc.; and an oxide thereof, and the like.

The catalyst may be supported on a carrier. The carrier may be used singly or in a combination of two or more selected from the group consisting of alumina, silica, titania, zirconia, magnesia, zeolite, etc.

The particle size of the catalyst is not particularly limited.

Also, as a fuel gas, methane and a hydrocarbon having about 2 to 5 carbon atoms, a mixture thereof, a natural gas, a methane prepared from coal and other substances, an LPG, etc., and an appropriate mixture thereof can be used. As an oxidizing agent, oxygen may be a pure oxygen, air, etc. As an auxiliary raw material, steam, water, carbon dioxide, etc. can be used. Also, nitrogen gas can be additionally used.

The reaction conditions for preparing the synthesis gas are such that the reaction is preferably carried out at the pressure of atmospheric pressure to 50 atm. Also, the preparation furnace (reactor) used for preparing the synthesis gas is not particularly limited.

Figure 9:
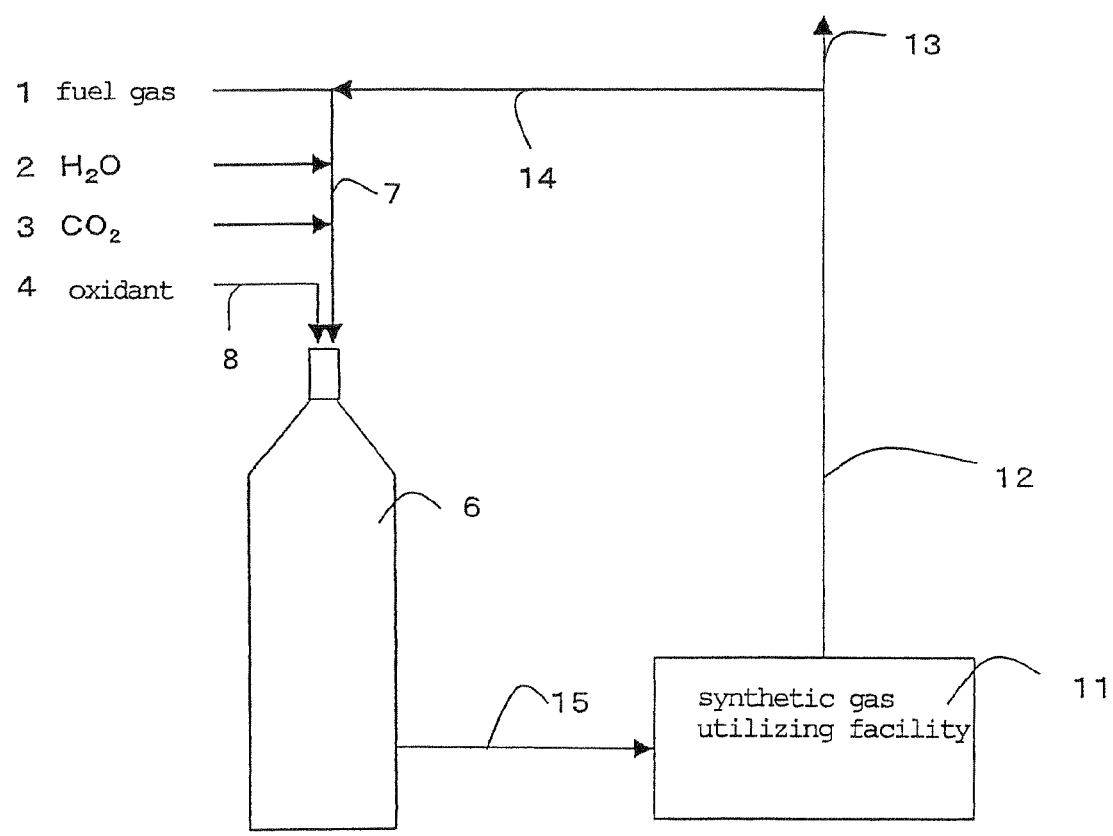
FIG. 9 is a schematic diagram showing a furnace for preparing a synthesis gas according to another embodiment of the present invention.

FIG. 9 is a schematic diagram showing another embodiment of the preparation furnace of the present invention.

In FIG. 9, the synthesis gas prepared by the preparation furnace (6) is used as a raw gas in a plant (11) using the synthesis gas. In the process of the plant (11) using the synthesis gas, an outlet gas containing carbon monoxide and hydrogen discharged from the reaction system is fed into the preparation furnace (6) as a portion of the raw material of the preparation furnace (6).

In the preparation furnace (6) of FIG. 9, a fuel gas (1) and an oxidizing agent (4) as raw materials are fed into the furnace (6) through a fuel gas feed line (7) and an oxidizing agent feed line (8), and a synthesis gas containing carbon monoxide and hydrogen is prepared in the presence of a catalyst. The synthesis gas discharged from a synthesis gas drain line (15) is fed into the plant (11) using the synthesis gas. In the process of the plant (11) using the synthesis gas, an outlet gas containing carbon monoxide and hydrogen discharged from the reaction system is discharged through a discharge line (12). A portion of the outlet gas is discharged from the discharge line to the outside of the system, and the remaining portion thereof is fed into the preparation furnace (6) through an outlet gas feeding line (14), which is connected to the fuel gas feeding line (7).

Also, herein, the process using the synthesis gas as the raw material is a preparation process by using a mixed gas containing hydrogen and carbon monoxide as raw materials. For example, the process may be the synthesis of DME, methanol, F-T, etc.

Also, as described above, the outlet gas containing carbon monoxide and hydrogen, discharged from the reaction system in the process using the synthesis gas as the raw material, is an unreacted gas which is not used in the reaction; an unreacted gas which is taken out to control the pressure of the reaction system; or an unreacted gas which is taken out for not increasing the concentration of the gas which is inert to the reaction by circulating in the reaction system.

EXAMPLE

A produced synthesis gas, or a purge gas of a DME synthesis reaction system was mixed with a raw material and introduced. The condition for this embodiment was such as to prepare a synthesis gas having the $H_2/CO$ ratio of 0.8 to 1.2. Under such condition, since the amount of the introduced steam was small, the gas excluding the condensed water was introduced. The outlet temperature of a catalyst layer was set at 1100 to 1300° C., and the synthesis gas was rapidly cooled to 600° C. or less in the lower part of the catalyst layer.

In Table 2, Comparative Examples 1 and 2 show examples of not circulating the synthesis gas, and Examples 1 and 2 show examples of circulating the synthesis gas.

It was found that in Examples 1 and 2, the amount of the introduced $CO_2$ in the raw gas could be lowered, and also the amount of $CO_2$ in the produced gas was decreased to 8 dry vol %. Since it is not easy to reduce the amount of $CO_2$ in a produced gas by even 1 dry vol %, the significance of the present invention is big.

TABLE 2

|  |  | Comparative Examples | | Examples | |
|---|---|---|---|---|---|
|  |  | 1 | 2 | 1 | 2 |
| Raw gas | Natural gas [$Nm^3/h$] | 400 | 400 | 400 | 400 |
|  | $O_2$ [$Nm^3/h$] | 342 | 328 | 354 | 340 |
|  | $CO_2$ [$Nm^3/h$] | 214 | 210 | 181 | 181 |
|  | $H_2O$ [$Nm^3/h$] | 21 | 0 | 0 | 0 |
|  | Circulating synthesis gas [$Nm^3/h$] | 0 | 0 | 219 | 225 |
| Component flux for circulating synthesis gas | CO [$Nm^3/h$] | 0 | 0 | 100 | 100 |
|  | $CO_2$ [$Nm^3/h$] | 0 | 0 | 19 | 19 |
|  | $H_2$ [$Nm^3/h$] | 0 | 0 | 100 | 106 |
| Outlet temp. of catalyst layer (T2) [° C.] | | 1200 | 1105 | 1206 | 1105 |
| Temp. after rapid cooling (T3) [° C.] | | 500 | 500 | 500 | 500 |
| Produced gas composition | CO [dry vol %] | 45.1 | 44.2 | 45.6 | 44.3 |
|  | $CO_2$ [dry vol %] | 9.8 | 9.3 | 8.5 | 8.5 |
|  | $H_2$ [dry vol %] | 45.1 | 46.5 | 45.8 | 47.2 |
|  | $CH_4$ [dry vol %] | 0.0 | 0.0 | 0.0 | 0.0 |

* 1: Pressure in the furnace: 0.6 MPa

<As to a Fourth Invention>
Twenty-Fifth Embodiment of the Present Invention

A method for preparing dimethyl ether, which comprises introducing a raw gas containing carbon monoxide and hydrogen into a reactor, and subjecting the raw gas to a catalytic reaction to produce dimethyl ether and at the same time to produce at least methanol as a by-product, wherein the purity of the produced methanol is increased to at least 95% by mass and the methanol with the increased purity is returned to the reactor.

Twenty-Sixth Embodiment of the Present Invention

A method for preparing dimethyl ether, which comprises introducing a raw gas containing carbon monoxide and hydrogen into a reactor, and subjecting the raw gas to a catalytic reaction to produce dimethyl ether and at the same time to produce at least methanol and water as by-products, wherein methanol is separated from a liquid containing the methanol and water obtained by cooling the produced gas from the reactor, and the separated methanol is returned to the reactor.

Twenty-Seventh Embodiment of the Present Invention

A method for preparing dimethyl ether, comprising introducing a raw gas containing carbon monoxide and hydrogen into a reactor and subjecting the raw gas to a catalytic reaction to produce dimethyl ether and at the same time to produce at least carbon dioxide, methanol and water as by-products, wherein the produced gas from the reactor is cooled to separate a liquid (1) containing dimethyl ether, carbon dioxide, methanol and water and a gas containing the unreacted gas component, carbon dioxide is separated from the obtained liquid (1), dimethyl ether is separated from a liquid (2) from which carbon dioxide is separated, methanol is separated from a liquid (3) from which carbon dioxide and dimethyl ether are separated, and the separated methanol is returned to the reactor.

Twenty-Eighth Embodiment of the Present Invention

The method for preparing dimethyl ether according to the twenty-seventh embodiment of the present invention, wherein the produced gas is contacted with the liquid (2) from which carbon dioxide is separated, and with the liquid (3) from which carbon dioxide and dimethyl ether are separated.

Twenty-Ninth Embodiment of the Present Invention

An apparatus for preparing dimethyl ether, which is provided with a reactor wherein a raw gas containing carbon monoxide and hydrogen is subjected to a catalytic reaction to produce dimethyl ether and at the same time to produce at least methanol as a by-product; a methanol purification apparatus wherein the purity of the produced methanol is increased to at least 95% by mass; and a recycling line wherein the purified methanol is returned to the reactor.

Thirtieth Embodiment of the Present Invention

An apparatus for preparing dimethyl ether, which is provided with a reactor wherein a raw gas containing carbon monoxide and hydrogen is subjected to a catalytic reaction to produce dimethyl ether and at the same time to produce at least carbon dioxide, methanol and water as by-products; a methanol purification apparatus for separating methanol from the liquid containing methanol and water obtained by cooling the produced gas from the reactor; and a recycling line wherein the separated methanol is returned to the reactor.

Thirty-First Embodiment of the Present Invention

An apparatus for preparing dimethyl ether, which is provided with a reactor wherein a raw gas containing carbon monoxide and hydrogen is subjected to a catalytic reaction to produce dimethyl ether and at the same time to produce at least carbon dioxide, methanol and water as by-products; a gas-liquid separation apparatus wherein the produced gas from the reactor is cooled to separate a liquid (1) containing carbon dioxide, dimethyl ether, methanol and water, and a gas containing the unreacted gas component; a $CO_2$ purification apparatus wherein carbon dioxide is separated from the obtained liquid (1); a DME purification apparatus wherein dimethyl ether is separated from a liquid (2) from which carbon dioxide is separated; a methanol purification apparatus wherein methanol is separated from a liquid (3) from which carbon dioxide and dimethyl ether are separated; and a recycling line wherein the separated methanol is returned to the reactor.

Thirty-Second Embodiment of the Present Invention

The apparatus for preparing dimethyl ether according to the thirty-first embodiment of the present invention, wherein in the gas-liquid separation apparatus, the produced gas is contacted with the liquid (2) from which carbon dioxide is separated by means of the $CO_2$ purification apparatus, and the liquid (3) from which dimethyl ether is separated by means of the DME purification apparatus.

[Technical Field]

The present invention relates to a method and an apparatus for preparing dimethyl ether, using carbon monoxide and hydrogen as main raw materials.

[Background Art]

As a technique for directly preparing dimethyl ether (DME) from a synthesis gas having carbon monoxide and hydrogen as main raw materials, a technique is disclosed, wherein a raw gas is reacted by passing through a slurry reactor in which a catalyst fine particles are suspended in a high-boiling medium oil, to synthesize dimethyl ether with a high yield. (See, for example, Patent Document 1).

In the method for directly synthesizing dimethyl ether from carbon monoxide and hydrogen, the three kinds of reactions as represented by each of the following formulae (1), (2) and (3), that is, the synthesis of methanol produced from hydrogen and carbon monoxide, the synthesis of dimethyl ether produced by the dehydration reaction from the synthesized methanol, and the production of hydrogen from the reaction of water with carbon monoxide which is produced through the synthesis of dimethyl ether, proceed at the same time, with satisfying each of the following formulae:

$$CO + 2H_2 \rightarrow CH_3OH \quad (1)$$

$$2CH_3OH \rightarrow CH_3OCH_3 + H_2O \quad (2)$$

$$H_2O + CO \rightarrow H_2 + CO_2 \quad (3).$$

In summarizing the formulae (1) to (3), dimethyl ether and carbon dioxide are produced in equal amounts from hydrogen and carbon monoxide, as represented by the following reaction formula (4):

$$3CO + 3H_2 \rightarrow CH_3OCH_3 + CO_2 \quad (4).$$

By the way, the reactions of the formulae (1) to (3) are equilibrium reactions, but in many cases, the introduced raw gas does not have sufficient time to reach an equilibrium state in the reactor, thus in the practical synthesis process, the three reactions as described above do not proceed to a 100% completion. Thus, the reaction of the overall formula (4) summarized from the three reactions as described above, does not proceed to a 100% completion. Therefore, there is no case where hydrogen and carbon monoxide as the raw materials are not 100% converted pursuant to the formula (4), and for the outlet gas from the reactor, methanol and water which are the intermediate reaction products are produced as the by-products, as well as DME and carbon dioxide as the reaction products. Furthermore, the outlet gas from the reactor comprises unreacted hydrogen and carbon monoxide.

Conventionally, after the produced methanol is separated from dimethyl ether, the methanol as a product is further purified or burned to be disposed of.

However, it was difficult for the methanol produced in a small amount to be commercially available as products from the dimethyl ether preparation plant constructed in a production site of natural gas or coal, and there has been a demand for the increased yield of dimethyl ether.

For this reason, the Applicant proposed a method for using the produced methanol effectively, wherein the liquid containing, as main components, methanol and water obtained by cooling the outlet gas from the reactor, is returned to the reactor, thus the yield of dimethyl ether is increased (See Patent Document 2).

[Patent Document 1] Japanese Unexamined Patent Application Publication No. 10-182528

[Patent Document 2] Japanese Unexamined Patent Application Publication No. 10-182529

[Disclosure of the Invention]

[Problems to be Solved by the Invention]

However, since it is difficult to separate a liquid containing methanol as a main component by regulating the cooling temperature, a liquid obtained by cooling unavoidably comprises dimethyl ether, water and carbon dioxide in addition to methanol. Table 3 represents the proportions of each of the components, methanol (MeOH), dimethyl ether (DME), water ($H_2O$) and carbon dioxide ($CO_2$) (relative to the whole amount of gas prior to cooling) which are carried to the recovered solution at 5 MPaG and 30° C.

TABLE 3

| MeOH | $H_2O$ | DME | $CO_2$ |
|---|---|---|---|
| 80 to 90% | 90 to 100% | 20 to 30% | 2 to 5% |

For dimethyl ether, 20 to 30% of the produced amount is liquefied at 30° C. Dimethyl ether, carbon dioxide and water as the reaction products, inhibit the reaction if they are returned to the reactor as they are. In the case where the components other than methanol are separated and discarded, dimethyl ether and carbon dioxide are lost (water may be discharged out of the system).

Furthermore, if water contained in the liquid is returned to the reactor, it inhibits the reaction, and the catalyst for dimethyl ether synthesis is deteriorated.

The present invention is directed to solve the problems as described above, and thus the object of the present invention is to provide a method for preparing dimethyl ether, thus it is possible to effectively use the methanol as a by-product and to increase the yield of dimethyl ether.

[Means to Solve the Problems]

In order to solve these problems, the thirty-third embodiment of the present invention is a method for preparing dimethyl ether, which comprises introducing a raw gas containing carbon monoxide and hydrogen into a reactor, and subjecting the raw gas to a catalytic reaction to produce dimethyl ether and at the same time to produce at least methanol as a by-product, wherein the purity of the produced methanol is increased to at least 95% by mass and the methanol having the increased purity is returned to the reactor.

The thirty-fourth embodiment of the present invention is a method for preparing dimethyl ether, which comprises introducing a raw gas containing carbon monoxide and hydrogen into a reactor, and subjecting the raw gas to a catalytic reaction to produce dimethyl ether and at the same time to produce at least methanol and water as by-products, wherein methanol is separated from a liquid containing methanol and water obtained by cooling the produced gas from the reactor, and the separated methanol is returned to the reactor.

The thirty-fifth embodiment of the present invention is a method for preparing dimethyl ether, comprising introducing a raw gas containing carbon monoxide and hydrogen into a reactor and subjecting the raw gas to a catalytic reaction to produce dimethyl ether and at the same time to produce at least carbon dioxide, methanol and water as by-products, wherein the produced gas from the reactor is cooled to separate a liquid (1) containing dimethyl ether, carbon dioxide, methanol and water and a gas containing the unreacted gas component, carbon dioxide is separated from the obtained liquid (1), dimethyl ether is separated from a liquid (2) from which carbon dioxide is separated, methanol is separated from a liquid (3) from which carbon dioxide and dimethyl ether are separated, and the separated methanol is returned to the reactor.

The thirty-sixth embodiment of the present invention is a method for preparing dimethyl ether according to the thirty-fifth embodiment of the present invention, wherein the produced gas is contacted with the liquid (2) from which carbon dioxide is separated, and with the liquid (3) from which carbon dioxide and dimethyl ether are separated.

The thirty-seventh embodiment of the present invention is an apparatus for preparing dimethyl ether, which is provided with a reactor wherein a raw gas containing carbon monoxide and hydrogen is subjected to a catalytic reaction to produce dimethyl ether and at the same time to produce at least methanol as a by-product; a methanol purification apparatus wherein the purity of the produced methanol is increased to at least 95% by mass; and a recycling line wherein the purified methanol is returned to the reactor.

The thirty-eighth embodiment of the present invention is an apparatus for preparing dimethyl ether, which is provided with a reactor wherein a raw gas containing carbon monoxide and hydrogen is subjected to a catalytic reaction to produce dimethyl ether and at the same time to produce at least carbon dioxide, methanol and water as by-products; a methanol purification apparatus for separating methanol from the liquid containing methanol and water obtained by cooling the produced gas from the reactor; and a recycling line wherein the separated methanol is returned to the reactor.

The thirty-ninth embodiment of the present invention is an apparatus for preparing dimethyl ether, which is provided with a reactor wherein a raw gas containing carbon monoxide and hydrogen is subjected to a catalytic reaction to produce dimethyl ether and at the same time to produce at least carbon dioxide, methanol and water as by-products; a gas-liquid separation apparatus wherein the produced gas from the reactor is cooled to separate a liquid (1) containing carbon dioxide, dimethyl ether, methanol and water, and a gas containing the unreacted gas component; a $CO_2$ purification apparatus wherein carbon dioxide is separated from the obtained liquid (1); a DME purification apparatus wherein dimethyl ether is separated from a liquid (2) from which carbon dioxide is separated; a methanol purification apparatus wherein methanol is separated from a liquid (3) from which carbon dioxide and dimethyl ether are separated; and a recycling line wherein the separated methanol is returned to the reactor.

The fortieth embodiment of the present invention is the apparatus for preparing dimethyl ether according to the thirty-ninth embodiment of the present invention, wherein in the gas-liquid separation apparatus, the produced gas is contacted with the liquid (2) from which carbon dioxide is separated by means of the $CO_2$ purification apparatus, and the liquid (3) from which dimethyl ether is separated by means of the DME purification apparatus.

[Effects of the Invention]

According to the present invention, it is possible to use methanol as a by-product effectively and to increase the yield of dimethyl ether. In addition, dimethyl ether, carbon dioxide and water as the reaction products, do not inhibit the reaction because the tendency that they are returned to the reactor is decreased.

Furthermore, according to the invention of the thirty-sixth embodiment of the present invention or the fortieth embodiment of the present invention, it is possible to increase the yield of dimethyl ether and carbon dioxide.

[Best Mode for Carrying Out the Invention]

Figure 10:
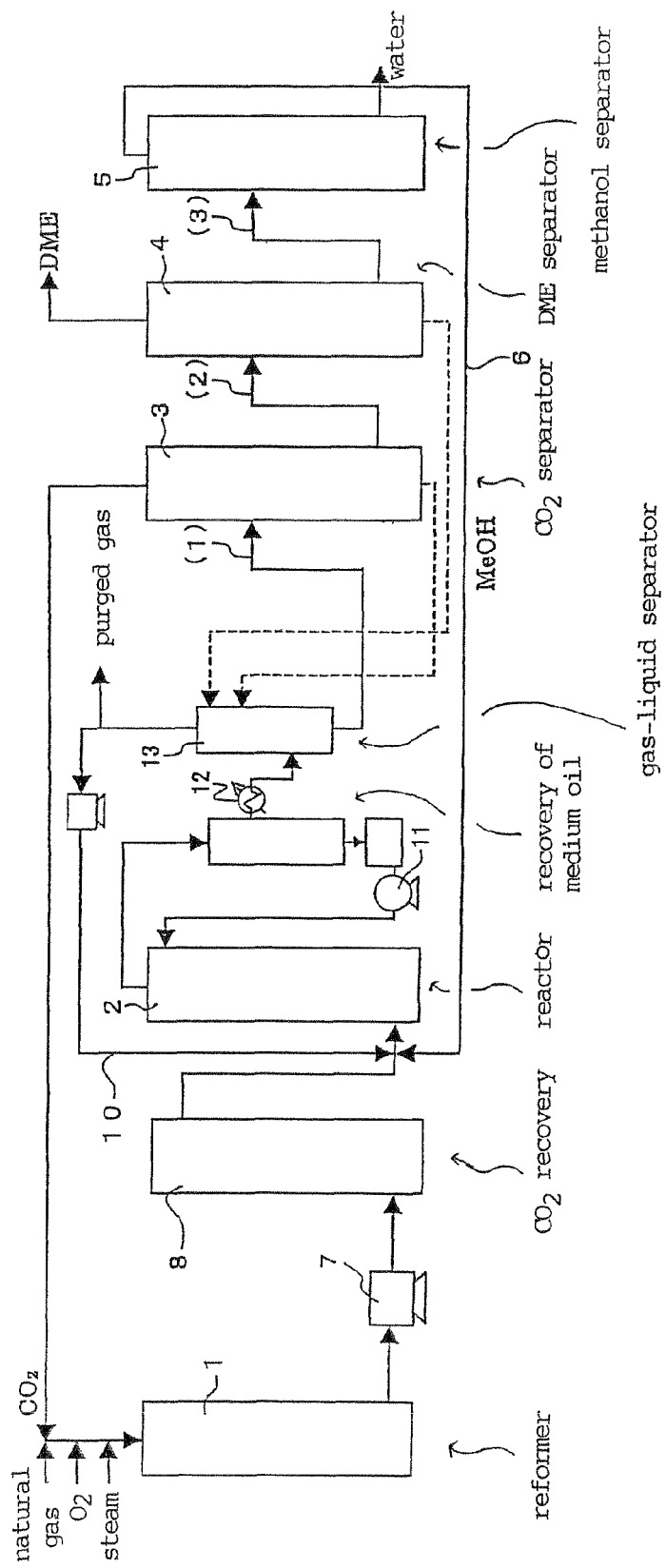
FIG. 10 is a flow diagram of an embodiment of an apparatus for manufacturing DME.

Hereinafter, the present invention will be described with reference to the Drawings. FIG. 10 shows an embodiment (a flow chart) of an apparatus for preparing dimethyl ether (hereinafter referred to as DME) of the present invention. In FIG. 10, (1) is a reformer for forming a carbon monoxide gas (hereinafter referred to as CO) and a hydrogen gas (hereinafter referred to as $H_2$) from a natural gas, and (2) is a DME synthesis reactor for producing dimethyl ether from a raw gas containing CO and $H_2$. From a liquid obtained by cooling the outlet reaction gas, from the reactor (2), carbon dioxide (hereinafter referred to as $CO_2$), DME and methanol (hereinafter referred to as MeOH) which are sequentially separated and purified in the three separation columns [(3), (4) and (5)], are separated and purified. The purified MeOH is returned to the reactor (2) through the recycling line (6).

Hereinafter, this apparatus will be explained along with a flow leading to the recovery of the purified and separated DME, which is passed from the reformer (1) through the reactor (2).

A natural gas is reacted with $CO_2$, $O_2$ and steam in the reformer (1) to produce a reforming reaction product. The reforming reaction product is cooled and dehydrated in the upstream of a synthesis gas compressor (7) (not shown in Figure), and the reforming product flowing out of the synthesis gas compressor (7) is decarbonated in a $CO_2$ recovery column (8).

The synthesis gas produced in the reformer (1) is dehydrated and decarbonated to be a raw gas for DME synthesis (a make-up gas for DME synthesis). Then, the make-up gas for DME synthesis is mixed with a recycling gas consisting mainly of the unreacted gas (CO and $H_2$) flowing through the recycle gas line (10), and MeOH flowing through the recycle gas line (6), to be a raw gas of DME).

The raw gas is fed from the bottom of the reactor (2). In the reactor (2), the raw materials are subjected to a catalytic reaction, thus the DME synthesis reaction proceeds. The medium oil flowing out of the reactor is recovered and returned to the reactor (2) by the pump (11).

Hereinafter, the reactor (2) will be described in detail. The type of the reactor (2) may be any one of a fixed-bed reactor, a fluidized-bed reactor and a slurry-bed reactor. Particularly, the slurry-bed reactor is preferable for the reason that the temperature inside the reactor is homogenous and the amount of by-products is low.

For a catalyst, a catalyst for methanol synthesis and methanol dehydration is used for DME synthesis by carrying out each of the reactions (1) to (3), and appropriately an aqueous shift reaction catalyst is suitably added. Catalysts having such functions are used in suitable combinations thereof appropriately.

As a methanol synthesis catalyst, there can be used copper oxide-zinc oxide, zinc oxide-chromium oxide, copper oxide-zinc oxide/chromium oxide, copper oxide-zinc oxide/alumina, etc. which are generally used in industry. As a methanol dehydration catalyst, there can be used alumina, silica, silica•alumina, zeolite, etc. which are an acid-base catalyst. Here, as a metal oxide component of zeolite, there can be used oxides of alkali metal, such as sodium and potassium, oxides of alkaline earth metal such as calcium and magnesium. Furthermore, since the methanol synthesis catalyst has strong shift catalytic activity, the catalyst can serve also as a water gas shift catalyst. As such catalyst having the combination of the methanol synthesis catalyst and the water gas shift catalyst, there can be used an alumina-supported copper oxide catalyst. The mixing ratio of the three kinds of catalyst as described above is not particularly limited, but it may be appropriately selected depending on the kind of the each component or the reaction conditions. However, in terms of the ratio by weight, generally about 0.1 to 5, preferably about 0.2 to 2 of the methanol dehydration catalyst is mixed, and about 0.2 to 5, preferably about 0.5 to 3 of the water gas shift catalyst is mixed, relative to the methanol synthesis catalyst. If the methanol synthesis catalyst and the water gas shift catalyst are identical materials and the methanol synthesis catalyst serves also as the water gas shift catalyst, the amount of the methanol synthesis catalyst to be used is the sum of the both catalysts.

For the catalyst form, in the case of using a slurry-bed reactor, a catalyst which is pulverized up to the average particle size of 300 μm or less, preferably 1 to 200 μm, more preferably 10 to 150 μm approximately, is used. In order to use the catalyst more effectively, a catalyst having the particle size as described above is used, which is obtained by compacting, molding and then re-pulverizing the mixed powder product.

A medium oil in the slurry-bed reactor should be one which maintains stably a liquid state under the reaction conditions. For example, aliphatic, aromatic and alicyclic hydrocarbons, alcohols, ethers, esters, ketones, halides or a mixture thereof are used. Although the amount of the catalyst in a solvent is suitably selected depending on kind of the solvent and the reaction conditions, but generally it is preferable that the amount is approximately 1 to 50% by weight, relative to the solvent.

As the reaction conditions in the slurry-bed reactor, the reaction temperature is preferably in the range of 150 to 400° C., particularly preferably in the range of 250 to 350° C. If the reaction temperature is below 150° C. or above 400° C., the CO conversion in the raw gas is low. The reaction pressure is preferably in the range of 10 to 300 $kg/cm^2G$, particularly preferably in the range of 20 to 70 $kg/cm^2G$. If the reaction pressure is below 10 $kg/cm^2G$, the CO conversion is low, while if the reaction pressure is above 300 $kg/cm^2G$, a particular reactor is required, as well as a large amount of energy is required for elevating the pressure, thus it is uneconomical. The space velocity (the feed rate of the raw gas under the standard state, per kg of the catalyst) is preferably 100 to 50000 Nl/kg·h, particularly preferably 500 to 7500 Nl/kg·h. If the space velocity is above 50000 Nl/kg·h, the CO conversion is low, while if the space velocity is below 100 Nl/kg·h, an extremely large reactor volume is required, thus it is uneconomical.

As such, the reaction gas obtained in the reactor 2, includes DME and $CO_2$ as the reaction products, $CH_3OH$ and $H_2O$ as the reaction intermediate products, the unreacted $H_2$ and CO, the impurities contained in the raw gas, and the like. The composition of the components of the raw gas is as follows: in general, DME: 3 to 25%, $CO_2$: 3 to 25%, CO: 20 to 50%, $H_2$: 20 to 50%, $CH_3OH$: 0.5 to 3%, $H_2O$: 0.1 to 0.5%, and others: approximately 5% or less.

Next, the gas produced from the reactor 2 is cooled by means of a heat exchanger 12, and is separated into the liquid (1) containing DME, $CO_2$, MeOH and $H_2O$, and the gas containing the unreacted gas components by means of a gas-liquid separator 13. The heat exchanger 12 and the gas-liquid separator 13 constitute a gas-liquid separation apparatus. By such cooling, the liquid (1) containing DME, MeOH and $H_2O$ is condensed, and $CO_2$ is dissolved in the condensed DME. Suitably, the cooling temperature is approximately –10° C. to –60° C., preferably approximately –40° C. to –50° C., and at this time the pressure is approximately 1 to 30 MPa, preferably approximately 1.5 to 15 MPa.

Figure 11:
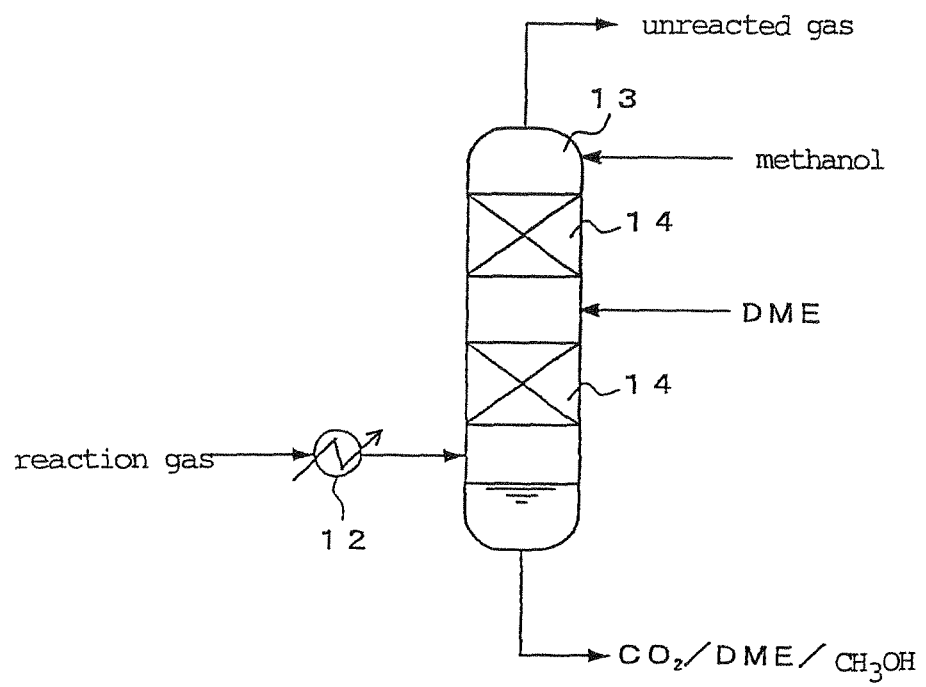
FIG. 11 is a detailed view showing a gas-liquid separator.

FIG. 11 represents a detailed chart of the gas-liquid separator 13. The gas-liquid separator 13 is connected to the outlet side of the heat exchanger 12 which is a condenser. Two layers comprising the packing materials 14, 14 such as Rasching ring are placed inside of the gas-liquid separator 13, and a solution reservoir is placed in the lower part. Nozzles are placed in the upper space of each layer of the packing materials 14, 14 so as to spray approximately uniformly on the top surface of the packing material layers. An inlet of the produced gas which is cooled in the heat exchanger, is formed in the space between the solution reservoir of the gas-liquid separator 13 and the lower-stage packing material layer 14; and an outlet of liquid-phase containing DME, $CO_2$ and MeOH, and an outlet of gas-phase containing the unreacted gas are provided at the lower part and the upper part, respectively. A methanol feed pipe is connected to the nozzles in the space above the upper-stage packing material layer 14, and a DME feed pipe is connected to the nozzles in the space above the lower-stage packing material layer 14.

From the nozzles of the gas-liquid separator 13, a bottom liquid of the $CO_2$ separation column 3 as described later (a liquid (2), that is crude DME, from which $CO_2$ is separated by the $CO_2$ separation column), and a bottom liquid of the DME separation column 4 as described later liquid (3), that is crude MeOH, from which DME is separated by the DME separation column) are sprayed, and the absorbed liquids are contacted with the produced gas. The crude DME and the crude MeOH can be fed at any time after or before the condensation of DME in the produced gas, but it is more efficient for them to supply such that they are contacted with the produced gas after the condensation, that is, the gas phase containing the unreacted gas. Any one of DME and MeOH may be fed beforehand and the other fed later, or they may be fed at the same time. Furthermore, they may be preliminarily mixed and then fed. However, in the case where the produced gas after the condensation of DME is treated using the absorption column as shown in FIG. 11, it is preferable to contact it with DME, and then MeOH to decrease the DME concentration in the discharged gas.

The bottom liquid (crude DME) in the $CO_2$ separation column and the bottom liquid (crude MeOH) in the DME separation column are contacted with the gas in the gas-liquid separator 13, thus to increase the recovery rate of $CO_2$ and DME. In order to decrease the DME concentration in the gas recycled into the reactor 2, MeOH not containing $CO_2$ and DME is needed. Since the presence of the DME separation column 4 allows the feed of a MeOH absorption liquid and the feed of MeOH not containing $CO_2$ and DME into the reactor, which leads to the increase in the amount of the recovered and produced DME.

The gas comprising an unreacted gas containing the separated CO and $H_2$ as main components, and a gas containing trace of impurity gas, is to be a recycled gas. Most of the gas passes through a recycle gas line 10 and is mixed with the make-up gas for DME synthesis. Thus, the mixed raw gas is fed from the bottom of the reactor 2.

The liquid (1) containing MeOH, $H_2O$, $CO_2$ and DME as main components is introduced into the $CO_2$ separation column 3 (the $CO_2$ purification apparatus) to, first, separate $CO_2$. In the $CO_2$ separation column 3, $CO_2$ is separated and purified, for example, by distillation.

In the $CO_2$ separation column 3, the liquid (2) from which $CO_2$ is separated, is introduced to the DME separation column 4 (the DME purification apparatus) to separate DME. In the DME separation column 4, DME is separated and purified, for example, by distillation. The high-purity DME after purification passes through the DME line, and is recovered as the product.

The liquid (3) from which $CO_2$ and DME are separated, comprises MeOH and $H_2O$ as main components. This liquid is introduced into the methanol separation column 5 (the methanol purification apparatus) to separate MeOH. In the methanol separation column 5, MeOH having a high purity of 96% by mass or more, is separated and purified, for example, by distillation. The separated, high-purity MeOH passes through the recycle line 6, is introduced to the make-up gas for DME synthesis and is evaporated. Thus, the raw gas with which MeOH is mixed is fed from the lower part of the reactor 2.

According to the present embodiments, since MeOH is purified and $H_2O$ is not introduced into the reactor 2, the catalyst is not deteriorated. Furthermore, since $H_2O$, $CO_2$ and DME are not introduced into the reactor, there is an advantage that the DME production reaction is not inhibited. In addition, an efficient process is accomplished, wherein the crude MeOH (3) is recycled into the gas-liquid separator 13, the high-purity MeOH is introduced into the reactor, and the MeOH is not discharged out of the system.

EXAMPLES

Figure 12:
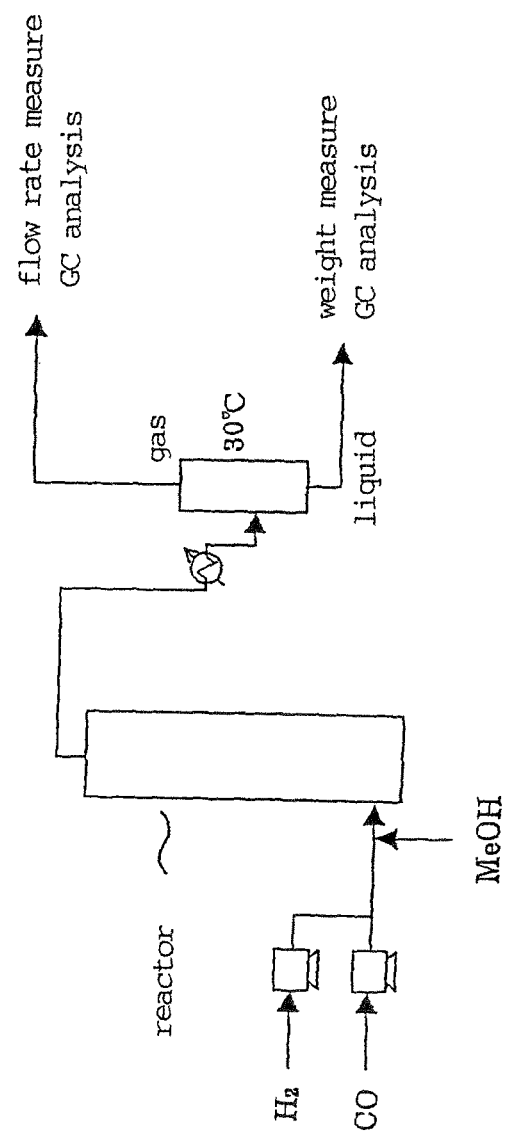
FIG. 12 is an experimental apparatus for determining the composition of a product when MeOH is returned to a reactor.

FIG. 12 represents an experimental apparatus to determine the composition of the product when MeOH is returned into the reactor. The experimental apparatus is in a scale smaller than the practical apparatus for preparing DME.

Into the reactor, CO and $H_2$ as a raw gas are fed. The slurry inside of the reactor consists of 388 g of the catalyst and 1552 g of a medium oil as shown in the following Table 4.

TABLE 4

| Slurry in the Reactor | |
|---|---|
| Catalyst | 388 g |
| Medium oil | 1552 g |

The reaction conditions in the reactor 2 are such that the temperature is 260° C. and the pressure is 5 MpaG, as shown in the following Table 5.

TABLE 5

| Reaction Conditions | |
|---|---|
| Temperature | 260° C. |
| Pressure | 5 MPaG |

The produced gas from the reactor is cooled at 30° C. in the heat exchanger, and is separated into the liquid containing MeOH and $H_2O$ as main components, and the gas containing the unreacted gas components, $CO_2$ and DME in the gas-liquid separator. The liquid recovered in the gas-liquid separator, was discharged through the reduced pressure valve, and volatilized $CO_2$ and DME under the normal pressure to obtain MeOH and $H_2O$ as liquid. For the gas produced under the reduced pressure, the flow rate was measured by means of a gas meter and then the composition was analyzed by means of a gas chromatograph. For the obtained liquid, the weight was measured, and then the composition was analyzed by means of a gas chromatograph. For the gas separated in the gas-liquid separator, the flow rate was measured by means of a gas meter and then the composition was analyzed by means of a gas chromatograph. In this experiment, the amount corresponding to the total amount of MeOH contained in the gas and the liquid obtained from the gas-liquid separator is returned into the reactor. Here, the raw gas was preheated at 110° C., and MeOH was preheated at 120° C.

In this experimental condition, MeOH sprayed in the raw gas was completely evaporated.

Furthermore, the flow rates of CO and $H_2$ fed into the reactor as the raw gas, are approximately 18 NL/min each. Thus, since the amount of the product is not sufficient for the stable operation of the distillation column, the distillation column is not provided.

Table 6 compares the composition of the products obtained in the case where MeOH is not introduced into the reactor (Comparative Examples) and the case where MeOH is introduced into the reactor (Examples).

TABLE 6

| | | Comparative Example | Example |
|---|---|---|---|
| Raw Material | $H_2$ [NL/min] | 18.11 | 18.11 |
| | CO [NL/min] | 18.11 | 18.11 |
| | MeOH [NL/min] | 0 | 0.456 |
| | MeOH Purity [%] | — | >99.8 |

TABLE 6-continued

|  |  | Comparative Example | Example |
|---|---|---|---|
| Product | $H_2$ [NL/min] | 8.36 | 8.41 |
|  | CO [NL/min] | 8.92 | 8.62 |
|  | $CO_2$ [NL/min] | 2.81 | 3.12 |
|  | DME [NL/min] | 2.96 | 3.32 |
|  | MeOH [NL/min] | 0.424 | 0.433 |
|  | $H_2O$ [NL/min] | 0.16 | 0.20 |
| MeOH Concentration in the Recovered Liquid under the Water-cooling [% by weight] |  | 81 | 78 |

The flow rates of $H_2$ and CO as the raw materials were measured by mass flow meters. MeOH was converted into the gas flow rate from the weight velocity of MeOH injected by a micro pump. The product was obtained from the results of the gas flow rate and the analysis by the gas chromatography, and the results of the measurement of the recovered liquid weight and the analysis of the gas chromatography. A "MeOH concentration in the recovered liquid under the water-cooling" is the MeOH concentration which is obtained by cooling the produced gas to 30° C. to recover the liquid, volatizing DME and $CO_2$ from the recovered liquid under the normal pressure, and then analyzing the remained $H_2O$ and MeOH by a gas chromatograph. 20 to 25% of the produced DME is also dissolved in the recovered liquid.

The flow rates of CO and $H_2$ as raw materials in both of Examples and Comparative Examples are set to be identical. In Examples, since the loading of the catalyst increases in proportion to the amount of the introduced MeOH, it was considered to attempt a reduction of the flow rates of CO and $H_2$ as raw materials. However, herein, the same flow rates as those of Comparative Examples were maintained. In Examples, increased flow rates of CO and $H_2$ in the products would indicate that there is any raw material not having changed into DME. However, the flow rates of CO and $H_2$ in the products did not change nearly at all. In the case where MeOH is introduced, the sum of the flow rate of CO plus that of $H_2$ in the product was found to be decreased. Moreover, the amount of DME among the products was increased as the amount of the introduced MeOH was increased, but the amount of MeOH in the products was not increased. In this experiment, all of methanol introduced into the reactor was converted inside the reactor. From this experiment, it was confirmed that since the flow rates of CO and $H_2$ as the introduced raw materials were not decreased and the flow rates of CO and $H_2$ in the products were not increased nearly at all, it was not necessary to increase the purge gas to be discarded.

That is, according to the experiment, although the whole amount of MeOH flowing out of the reactor 2 was introduced, the conversions of CO and $H_2$ did not change nearly at all, and the amount of DME corresponding to that of the introduced MeOH was increased. Meanwhile, the amount of MeOH flowing out of the reactor 2 remains almost unchanged. In addition, although the amount of MeOH equal to or more than the amount to be discharged was introduced, the amount of DME corresponding to the introduced amount of MeOH was increased. As such, since the excess MeOH can be treated in the reactor, it is possible to treat MeOH introduced from the outside of the system.

It was also considered that since MeOH is an intermediate product of the DME synthesis reaction, introduction of MeOH would inhibit the reaction and hence would not increase the yield of DME. In other words, it was considered that there is limitation to the amount of DME produced in the reactor, and that as MeOH is introduced, CO and $H_2$ would not react and remain as an unreacted gas. However, it has been shown that, when MeOH is introduced from the inlet of the reactor, the amount of the prepared DME is increased, even using the same amount of the catalyst.

It is believed that this is because the methanol dehydration catalyst at the bottom of the reactor 2 has an excess catalytic capability, which is effectively used. The slurry-bed reactor 2 is vertically long in structure, and has the portions performing the reactions represented by the formulae (1) to (3) at the upper side and the lower portions. At the lower portion of the reactor 2, $H_2$ and CO are reacted to produce MeOH according to the reaction formula (1), however, it is possible that the dehydration catalyst performing the reaction of the formula (2) and the shift catalyst performing the reaction of the formula (3) are not activated. It is considered that, if MeOH is introduced into the lower portion of the reactor 2, the reactions of the formulae (2) and (3) proceed by the dehydration catalyst and the shift catalyst, thus the amount of the prepared DME is increased.

Figure 13:
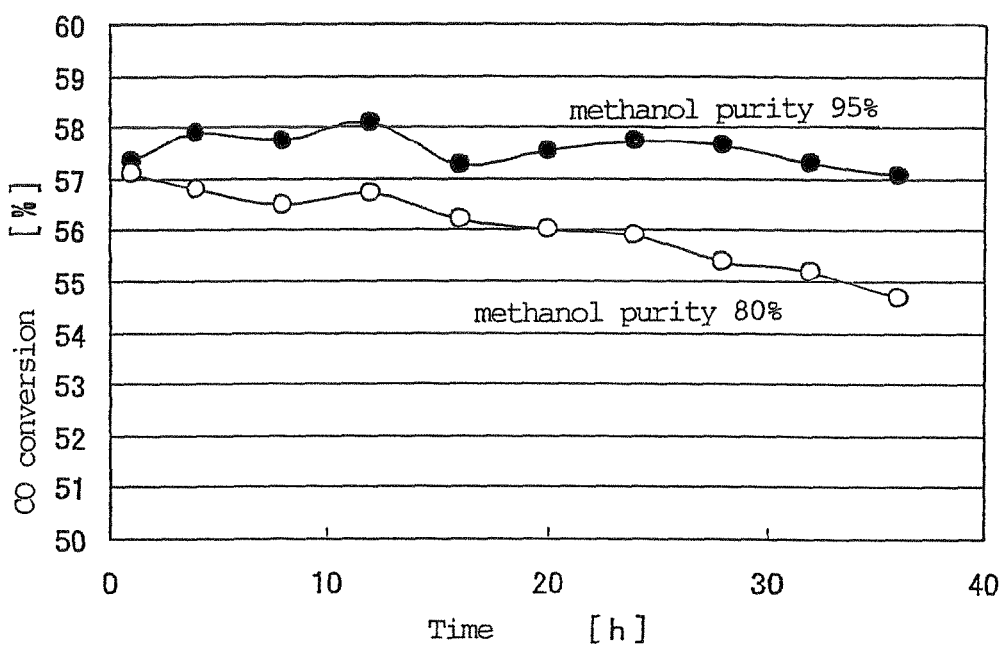
FIG. 13 is a graph showing a temporal variation in CO conversion when the purity of MeOH is changed.

FIG. 13 is a graph showing the change of the CO conversion over time in the case where the purity of MeOH introduced into the reactor 2 is changed. MeOH having a predetermined purity was prepared by adding distilled water ($H_2O$) to MeOH. The amount of the introduced raw material is the same as in Examples. However, the amount of MeOH was set as the amount of MeOH in $H_2O$+MeOH. The amount of the introduced raw material is the same as in Examples. If the purity of MeOH is decreased, the flow rates of $H_2$, CO and MeOH are not changed, but the amount of $H_2O$ is increased. The value of CO conversion indicates how much CO as a raw material is converted into the product. It was confirmed that if the MeOH purity is 95% by mass, the CO conversion did not decrease nearly at all, while if the MeOH purity is 80% by mass, the CO conversion decreased slightly. That is, with 95% by mass of the MeOH purity, the change over time is negligible, while with 80% by weight of the MeOH purity, the deterioration over time is not negligible.

Further, various modifications can be made in the present invention without limiting to the above embodiment. For example, the present invention is not limited to the method wherein the equal amounts of DME and $CO_2$ are produced, using the overall formula (4), but it covers the general methods wherein MeOH is produced as a by-product while synthesizing DME.

Furthermore, in the embodiments as described above, the liquid containing DME, $CO_2$, MeOH and $H_2$, and the gas containing unreacted gas components are separated by means of the one-stage gas-liquid separation device, but they may be separated by means of a two-stage gas-liquid separation device. In this case, first, the produced gas is cooled to approximately 30° C. in the first stage of the gas-liquid separation device to obtain a liquid containing MeOH and $H_2O$ as main components. Next, the produced gas is cooled to approximately −30 to −50° C. in the second stage of the gas-liquid separation device to obtain a DME liquid having $CO_2$ dissolved therein. Further, MeOH is purified from the liquid containing MeOH and $H_2O$ as main components, which is separated in the first stage of the gas-liquid separation device, and then the MeOH may be returned into the reactor.

<As to a Fifth Invention>

Forty-First Embodiment of the Present Invention

A medium oil which is used for the synthesis reaction with a slurry-bed reaction procedure as a medium, comprising, as a main component, a branched, saturated aliphatic hydrocarbon having 16 to 50 carbon atoms, 1 to 7 tertiary carbon atoms, 0 quaternary carbon atom, and 1 to 16 carbon atoms in the branched chains bonded to the tertiary carbon atoms; and at least one of the tertiary carbon atoms being bonded to hydrocarbon chains with a chain length having 4 or more of carbon atoms in three directions.

Forty-Second Embodiment of the Present Invention

The medium oil which is used for the slurry-bed reaction procedure according to the forty-first embodiment of the present invention wherein the branched, saturated aliphatic hydrocarbon has 20 to 40 carbon atoms and 1 to 4 tertiary carbon atoms.

Forty-Third Embodiment of the Present Invention

The medium oil which is used for the slurry-bed reaction procedure according to the forty-first or the forty-second embodiments of the present invention wherein the branched, saturated aliphatic hydrocarbon is represented by formula (I):

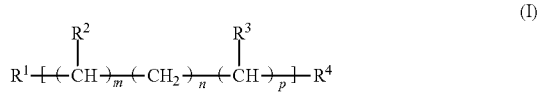

wherein, $R^1$, $R^2$ and $R^4$ are independently n- or iso-alkyl group having 4 to 16 carbon atoms, $R^3$ is a n- or iso-alkyl group having 1 to 3 carbon atoms, m is an integer in a range of 1 to 7, n is an integer in a range of 0 to 37, and p is an integer in a range of 0 to 12, provided that —($CR^2H$)—, —($CH_2$)— and —($CR^3H$)— in [ ] are bonded in any order and the total numbers of each unit are m, n and p, respectively.

Forty-Fourth Embodiment of the Present Invention

The medium oil which is used for the slurry-bed reaction procedure according to any one of the forty-first to the forty-third embodiments of the present invention wherein the branched, saturated aliphatic hydrocarbon is any one of dimers to octamers of α-olefins having 6 to 18 carbon atoms.

Forty-Fifth Embodiment of the Present Invention

The medium oil which is used for the slurry-bed reaction procedure according to any one of the forty-first to the forty-fourth embodiments of the present invention, which has a pour point of −10° C. or lower.

Forty-Sixth Embodiment of the Present Invention

The medium oil which is used for the slurry-bed reaction procedure according to any one of the forty-first to the forty-fifth embodiments of the present invention wherein the synthesis reaction with the slurry-bed reaction procedure comprises producing an oxygen-containing organic compound from a raw gas containing carbon monoxide and hydrogen.

Forty-Seventh Embodiment of the Present Invention

The medium oil which is used for the slurry-bed reaction procedure according to the forty-sixth embodiment of the present invention wherein the oxygen-containing organic compound is usually dimethyl ether.

Forty-Eighth Embodiment of the Present Invention

A process for preparing dimethyl ether, comprising passing a raw gas containing carbon monoxide and hydrogen through a catalyst slurry containing a mixture comprising (1) the medium oil described in any one of the forty-first to the forty-seventh embodiments of the present invention, (2) a methanol synthesis catalyst and (3) a methanol dehydration catalyst and a methanol shift catalyst, or a methanol dehydration/shift catalyst.

Forty-Ninth Embodiment of the Present Invention

A process for preparing a mixture of dimethyl ether and methanol comprising passing a raw gas containing carbon monoxide and hydrogen through a catalyst slurry containing a mixture comprising (1) the medium oil described in any one of the forty-first to the forty-seventh embodiments of the present invention, (2) a methanol synthesis catalyst and (3) a methanol dehydration catalyst and a methanol shift catalyst or a methanol dehydration/shift catalyst.

[Field of the Invention]

The present invention relates to a medium oil used for a slurry-bed reaction and a process for preparation of dimethyl ether.

As used herein, the term "medium oil" is, for example, a liquid used as a medium in a slurry-bed reactor (sometime, so-called a suspension bubble column reactor or gas-liquid-solid mixed-flow reactor) which means the liquid (at least including a material in liquid state under a reaction condition desired) capable forming a catalytic slurry as a mixture of the solid catalyst introduced in the reactor and the liquid described above.

[Background Art]

Conventionally, dimethyl ether has been prepared by means of methanol dehydration, generally using methanol as a raw material, but recently, a process for directly synthesizing dimethyl ether from a raw gas containing carbon monoxide and hydrogen has been developed.

In such a process, the synthesis of dimethyl ether is accomplished by a reaction represented by the following reaction formulae (1) and (2) in the presence of a methanol dehydration catalyst (that is, a methanol conversion catalyst) such as alumina etc. First, methanol is produced from carbon monoxide and hydrogen by a methanol synthesis catalyst, followed by dehydration and condensation of the produced methanol by a methanol dehydration catalyst to produce dimethyl ether and water. The produced water further reacts with carbon monoxide according to the reaction formula (3) to give carbon dioxide and hydrogen.

[Reaction Formula 2]

$$CO + 2H_2 \rightarrow CH_3OH \qquad (1)$$

$$2CH_3OH \rightarrow CH_3OCH_3 + H_2O \qquad (2)$$

$$H_2O + CO \rightarrow CO_2 + H_2 \qquad (3)$$

The above synthesis is a strong exothermic reaction, and has a problem that the catalyst used may be deactivated due to high temperatures.

For this reason, it has been noted to study the synthesis of dimethyl ether by means of a slurry-bed reaction procedure which can effectively remove the reaction heat in great quantities and easily control the temperature.

In such a slurry-bed reaction procedure, used is a catalyst slurry prepared by suspending a catalyst in a suitable medium oil. The medium oil used in the above procedure must satisfy some performances, for example, such as (1) that it has high stability, that is, it is inactive for the reaction, does not change over time, and is neither thermally polymerized and thermally decomposed, nor reductively decomposed; (2) that it has high solubility of a raw gas such as CO, 2$H_2$; (3) that it has a high boiling point; and (4) that it has a low freezing point.

The process for preparing dimethyl ether using a slurry-bed reactor is disclosed, for example, in Patent Document 1 by Air Products and Chemicals, Inc. In this process, the medium oil used in forming the catalyst slurry within the reactor includes, for example, paraffin-based hydrocarbons or mixture thereof, and in Examples of the document, a medium oil purified from a natural mineral oil referred to as "Witco 70" is used. Air Products and Chemical, Inc. also reports the synthesis of dimethyl ether using the slurry-bed procedure wherein a purified natural mineral oil, referred to as Drakeol 10 is used as a medium oil in Non-Patent Document 1.

In addition, Patent Document 2 by Sunggyu Lee et al., discloses the synthesis of gasoline components as a light oil through dimethyl ether from hydrogen and carbon monoxide as raw materials and using a slurry-bed reactor. In this case, employed are medium oils derived from natural mineral oils such as Witco 40, Witco 70 or Freezene 100, etc. Similarly, the synthesis of dimethyl ether using slurry-bed procedure in which Witco 40 or Witco 70 is used as a medium oil is disclosed in the documents other than Non-Patent Document 2.

For the above medium oils, referred to as Witch 40, Witch 70, Freezene 100 and Drakeol 10, the present inventors conducted a ring analysis using n-d-M method (ASTM D 3238), and as a result, it was found that % $C_P$ (the percent of the number of paraffinic carbon atoms relative to the total number of carbon atoms) is below 70. Additionally, the result of analysis for molecular structures of Witch 40, Witco 70, Freezene 100 and Drakeol 10 by means of NMR, etc. indicated that the fraction of carbon atoms having branches, namely, the number of carbon atoms having not less than 3 carbon-carbon bonds are not less than 20% of the total number of carbon atoms.

Such conventional medium oils derived from natural mineral oils by purification have a problem that the synthesis efficiency of dimethyl ether gets lower over time. More particularly, as described in Non-Patent Document 1, the slurry-bed synthesis of dimethyl ether using Drakeol 10 causes remarkable decrease in the amount of dimethyl ether produced over time, thereby, resulting in decrease in the amount of the produced dimethyl ether approximately by a half in about 500 hours. In addition to Drakeol 10, in the case of the slurry-bed synthesis of dimethyl ether using generally known medium oils such as Witco 70 or Freezene 100, etc., it was found that the amount of the produced dimethyl ether was noticeably decreased over time. Further, when the natural mineral oil is thermally decomposed at high temperatures, it cannot avoid the generation of carbon residues. That is, if such natural mineral oil is employed as the medium oil, the catalyst may be deactivated due to coking process of the medium oil. Also, generally it needs an appropriate level of fluidity for the medium oil at a desired temperature in view of handling the medium oil.

Under the above circumstances, the present inventors intensively studied to solve the problems and proposed a medium oil used in preparing an oxygen-containing organic compound of which dimethyl ether is representative, which comprises a hydrocarbon as a main component and has 70% or more of paraffinic carbon atoms, relative to the total number of carbon atoms in Patent Document 3. Representative example of the above medium oil includes polybutene obtained by copolymerizing isobutene and n-butene as main components.

[Patent Document 1] Japanese Examined Patent Application Publication No. 07-057739
[Patent Document 2] U.S. Pat. No. 5,459,166
[Patent Document 3] Japanese Unexamined Patent Application Publication No. 2000-109437
[Non-Patent Document 1] USA DOE report, DOE/PC/89865-T6 (September, 1992)
[Non-Patent Document 2] Sunggyu Lee, et al. "A Single-Stage, Liquid-Phase Dimethyl Ether Synthesis Process from Syngas I. Dual Catalytic Activity and Process Feasibility", Fuel Science and Technology Int'l, 9(6), 653-679 (1991).

Disclosure of the Invention

Problems to be Solved by the Invention

A medium oil such as polybutene disclosed in Patent Document 3 has high thermal stability and a low freezing point, and ensures high reactivity for the synthesis of, for example, dimethyl ether as a medium oil, as compared to the conventional medium oils derived from natural mineral oils.

However, it was found that the medium oil disclosed in the above document was decomposed, volatilized and, thus decreased in the amount slowly over time.

Accordingly, the present invention has an object to provide a medium oil having high reactivity for the synthesis of for example dimethyl ether etc., as a medium oil having a high boiling point, a low freezing point and excellent stability.

Means for Solving the Problems

In order to solve the above problems, the present invention has an object to provide a medium oil used as a medium for the synthesis with a slurry-bed reaction procedure, which comprises, as a main component, a branched, saturated aliphatic hydrocarbon having 16 to 50 carbon atoms, 1 to 7 tertiary carbon atoms, 0 quaternary carbon atom, and 1 to 16 carbon atoms in branched chains bonded to the tertiary carbon atoms; and at least one of the tertiary carbon atoms being bonded to hydrocarbon chains with a chain length having 4 or more of carbon atoms in three directions.

The medium oil for the slurry-bed reaction procedure of the present invention preferably comprises a branched, saturated aliphatic hydrocarbon having 20 to 40 carbon atoms and 1 to 4 tertiary carbon atoms. The branched, saturated aliphatic hydrocarbon of the present invention is represented by formula (1)

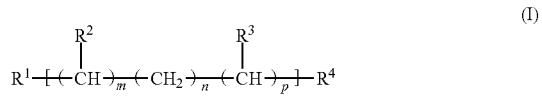

wherein $R^1$, $R^2$ and $R^4$ are independently n- or iso-alkyl groups having 4 to 16 carbon atoms, $R^3$ is a n- or iso-alkyl group having 1 to 3 carbon atoms, m is an integer in a range of 1 to 7, n is an integer in a range of 0 to 37, and p is an integer in a range of 0 to 12, provided that —($CR^2H$)—, —($CH_2$)— and —($CR^3H$)— in [ ] are bonded in any order and the total numbers of each unit are m, n and p, respectively. The branched, saturated aliphatic hydrocarbon of the medium oil is any one of dimers to octamers of α-olefins having 6 to 18 carbon atoms.

The medium oil for the slurry-bed reaction procedure of the present invention preferably a pour point of −10° C. or lower.

Also, in the present invention relates, an oxygen-containing organic compound from a raw gas containing carbon monoxide and hydrogen, more particularly, dimethyl ether is prepared through the synthesis reaction with the slurry-bed reaction procedure.

An object of the present invention to solve the above problems, is a process for preparing dimethyl ether, which comprises passing a raw gas containing carbon monoxide and hydrogen through a catalyst slurry containing a mixture comprising (1) a medium oil for the slurry-bed reaction procedure as described above, as a medium oil, (2) a methanol synthesis catalyst and (3) a methanol dehydration catalyst and shift catalyst, or a methanol dehydration/shift catalyst.

Another object of the present invention to solve the above problems, is a process for preparing a mixture of dimethyl ether and methanol, which comprises passing a raw gas containing carbon monoxide and hydrogen through a catalyst slurry containing a mixture comprising (1) a medium oil for the slurry-bed reaction procedure as described above, as a medium oil, (2) a methanol synthesis catalyst and (3) a methanol dehydration catalyst and shift catalyst or a methanol dehydration/shift catalyst.

Effects of the Invention

By the medium oil according to the present invention, it is possible to enhance the synthesis efficiency of an oxygen-containing organic compound such as dimethyl ether and keep the synthesis efficiency for a long time and, at the same time, to stably use the medium oil for a long time without decomposition, volatilization or the like over time. Therefore, the present invention has a remarkable advantage in preparing the oxygen-containing organic compound such as dimethyl ether requiring a high production efficiency.

Best Mode for Carrying Out the Invention

The present invention will be described in detail with reference to the following examples.

The medium oil for the synthesis reaction with the slurry-bed reaction procedure according to the present invention comprises, as a main component, a branched, saturated aliphatic hydrocarbon having 16 to 50 carbon atoms, 1 to 7 tertiary carbon atoms, 0 quaternary carbon atom and 1 to 16 carbon atoms in branched chains bonded to the tertiary carbon atoms; and at least one of the tertiary carbon atoms being bonded to hydrocarbon chains with a chain length having 4 or more of carbon atoms.

As used herein, the term "a main component" means a component contained by not less than 70% by weight, preferably not less than 90% by weight in the medium oil.

In the medium oil of the present invention, the branched, saturated aliphatic hydrocarbon as the main component has 16 to 50 carbon atoms. If the number of the carbon atoms is less than 16, the boiling point of the hydrocarbon is lowered, thus to cause, for example, the hydrocarbon with desired properties not to be obtained. While if the number of the carbon atoms exceeds 50, the solubility of the raw gas may be not sufficient. The branched, saturated aliphatic hydrocarbon has more preferably 20 to 40, and most preferably 30 to 40 carbon atoms, although it depends on the molecular structure of the hydrocarbon.

The number of tertiary carbon atoms ranges from 1 to 7. When the number of the tertiary carbon atoms is 0, with the hydrocarbon having the total number of carbon atoms ranging from 16 to 50, the freezing point increases and in turn the hydrocarbon is solidified at ambient temperature, thereby resulting in difficulty in handling the medium oil. If the number of the tertiary carbon atoms exceeds 7, the molecular stability is gradually reduced to cause easily decomposition or polymerization thereof, and if the number of the branched chains is increased, the liquid viscosity is increased. As the liquid viscosity is increased, not only is increased the resistance of the liquid upon flowing it, but also is increased the diameter of bubbles dispersed in the slurry-bed reactor to cause reduction of gas hold-up and reduction of reactivity, thus it is undesirable. The number of tertiary carbon atoms ranges preferably from 1 to 4, more preferably from 1 to 3.

The medium oil of the present invention has no quaternary carbon atom. If the quaternary carbon atom is contained in the medium oil, as in the polybutene medium oil described in Patent Document 3, it causes thermal decomposition over time, thus to result in a trouble in view of stability. Since the quaternary carbon induces easily dissociation of intramolecular bonds compared to the tertiary carbon, it is preferable to construct the desired branched chains with the tertiary carbon.

In the medium oil of the present invention, the number of carbon atoms in the branched chains binding to the tertiary carbon atom ranges generally from 1 to 16. If the number of the carbon atoms exceeds 16, the total number of carbon atoms exceeds 50. Herein, the main chain is the longest carbon chain in one molecule while the branched chain is the carbon chain branched from the main chain.

Further, in the medium oil of the present invention, at least one tertiary carbon is bonded to a hydrocarbon chain having 4 or more of carbon atoms in three directions. With such molecular structure, it is possible to extend the temperature range in which a liquid state exists between the pour point and the boiling point with the least branched chains. Since the dissociation of the intramolecular bonds is easily induced at the branched portion, it is preferable to make the branching as small as possible. The tertiary carbon is preferably bonded to the hydrocarbon chain having 8 or more of carbon atoms in three directions.

Such branched, saturated aliphatic hydrocarbon in the medium oil according to the present invention includes, but is not limited to, the compound represented by the following formula (I):

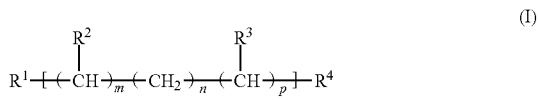

(I)

wherein $R^1$, $R^2$ and $R^4$ are independently n- or iso-alkyl groups having 4 to 16 carbon atoms, $R^3$ is a n- or iso-alkyl group having 1 to 3 carbon atoms, m is an integer in a range of 1 to 7, n is an integer in a range of 0 to 37, and p is an integer in a range of 0 to 12, provided that —($CR^2H$)—, —($CH_2$)— and —($CR^3H$)— in [ ] are bonded in any order and the total numbers of each unit are m, n and p, respectively.

In the above formula (1), $R^1$, $R^2$ and $R^3$ include, for example, particularly n-hexyl, n-pentyl, ethylhexyl, n-octyl, n-nonyl and n-decyl groups but are not limited thereto.

Also, in the above formula (1), $R^4$ includes, for example, particularly methyl, ethyl, n-propyl and isopropyl groups but is not limited thereto.

The medium oil of the present invention can further include the conventionally known medium oil as a minor component (for example, the medium oil described in the above section [BACKGROUND OF THE RELATED ART]), in addition to the branched, saturated aliphatic hydrocarbon as the main component. Furthermore, the medium oil of the present invention can comprise a hydrocarbon containing impurities such as oxygen, nitrogen, silicon and halogen, and the like, in addition to the above main component and minor components. Still further, as the main component, the branched, saturated aliphatic hydrocarbon can be employed in a combination of 2 or more of different kinds of the hydrocarbon.

The medium oil of the present invention may be derived from synthetic oil or natural oil raw materials but, preferably from the synthetic materials.

In order to prepare the medium oil of the present invention having the above characteristics, there are proposed a method for separating paraffin from a natural oil using adsorption on a molecular sieve; a separation process using distillation or a combination of distillation and extraction by a solvent; a hydrogenation method of the natural oil; a synthesis process using a process with product selectivity (that is, selectivity for paraffin) such as Fischer-Tropsch synthesis, etc.; or a process of polymerization and/or copolymerization of α-olefin.

The polymerization or copolymerization process of the α-olefin includes, but is not limited to, a process for obtaining dimmers to octamers of the α-olefin having 6 to 18 carbon atoms, more preferably dimmers to pentamers of the α-olefin having 8 to 12 carbon atoms such as 1-octene, 1-decene, 1-dodecene, etc. One of the most preferable examples may be, for example, poly-1-decene (a trimer).

The polymerization or copolymerization of the α-olefin can be performed in the presence of a polymerization catalyst such as Friedel-Crafts catalyst including, for example, complexes comprising aluminum trichloride, boron trifluoride or boron trichloride and water, alcohols such as ethanol, propanol or butanol, or esters such as ethyl acetate or ethyl propionate.

Also, the Fischer-Tropsch synthesis is a method to synthesize a liquid hydrocarbon by the reaction of carbon monoxide and hydrogen in the presence of a catalyst (for example, an iron-, cobalt- or nickel-based catalyst, or a ruthenium catalyst).

The branched, saturated aliphatic hydrocarbon according to the present invention satisfying the reaction conditions described above does not release hydrogen, decompose or polymerize even at a temperature as high as about 300° C. Accordingly, in contrast with conventionally known natural mineral oils used as the medium oil, the medium oil of the present invention does not leave carbon residues as a result of thermal decomposition at high temperatures. Also, the catalyst used in the present invention is scarcely deactivated by the coking process.

In the medium oil of the present invention, the percentage of the saturated aliphatic hydrocarbon in the medium oil (% $C_P$) with respect to the total number of carbon atoms in the medium oil (namely, the sum of the number of carbon atoms of the main component hydrocarbon plus the number of carbon atoms of minor components) is 70% or more, preferably 80% or more. When % cP of the medium oil is less than 70%, it may not be sometimes possible to maintain the synthesis efficiency of the oxygen-containing organic compound for a long time.

The content of the saturated aliphatic hydrocarbon in the medium oil, relative to the total number of carbon atoms of the medium oil, can be determined by the following analysis procedures, without limitation thereto, including, for example, a ring analysis using an n-d-M method (ASTM D 3238). The content of the saturated aliphatic hydrocarbon in the present description is a value determined by the n-d-M method. The term "ring analysis" means a method to analyze the assignment of carbon atoms (such as % $C_A$, % $C_N$, % $C_R$, % $C_P$) in all of the compounds constituting an oil (that is, an oil composition and/or an oil mixture) from a computational formula predetermined based on physical and chemical properties of the oil. Herein, % $C_A$ is a percentage of aromatic carbon atoms contained in the oil to be analyzed, based on the total carbon atoms in the above oil (that is, the number of carbon atoms constituting the aromatic ring), % $C_N$ is a percentage of naphthenic carbon atoms contained in the oil to be analyzed, based on the total carbon atoms in the above oil (that is, the number of carbon atoms constituting the alicyclic ring), % $C_R$ is a percentage of aromatic carbon atoms and naphthenic carbon atoms contained in the oil to be analyzed, based on the total carbon atoms in the above oil, and % $C_P$ is a percentage of paraffin carbon atoms contained in the oil to be analyzed, based on the total carbon atoms in the above oil (that is, the number of carbon atoms constituting the saturated aliphatic hydrocarbon chain). In the medium oil of the present invention, most of the aliphatic hydrocarbons are paraffin based hydrocarbons and unsaturated aliphatic hydrocarbons are not contained nearly at all, thus % $C_A$+% $C_N$+% $C_P$=100 or % $C_R$+% $C_P$=100.

The medium oil of the present invention has a weight average molecular weight ranging from 200 to 800 without limitation thereto, more preferably from 280 to 600 and most preferably from 400 to 600. If the weight average molecular weight is less than 170, the amount of the medium oil to be evaporated is too much, and thus the capacity of a trap for the evaporated medium oil provided downstream of the reactor or the capacity of an oil recycling pump is increased. For this reason, the plant cost is increased. Also, it sometimes is difficult to control the oil amount in the reactor, in turn, to control the temperature. On the other hand, when the weight average molecular weight of the medium oil exceeds 800, the viscosity of the oil is increased while the solubility of CO or $H_2$ is decreased, thus to cause the decrease of reaction efficiency of the synthesis process. The weight average molecular weight of the medium oil of the present invention can be determined, for example, by means of mass spectroscopy or gel-permeation chromatography.

The pour point of the medium oil according to the present invention is not particularly limited, but is preferably −10° C. or less, more preferably −20° C. or less and, most preferably −30° C. or less. If the pour point is higher than −10° C., the medium oil may be frozen at ambient temperature or at general temperatures in winter. For this reason, the plant cost may be increased because additional treatments such as keeping pipelines warm are required, or it is difficult to conduct working itself such as oil handling. Moreover, in the case of dissolving $CO_2$ as a by-product in DME generated by the DME synthesis reaction, it is effective to cool the generated gas in a cooler to −20° C. or lower. However, since there is a risk that the cooler may be closed when the vaporized medium oil is carried over to the cooler, the pour point is preferably −20° C. or lower, and more preferably −30° C. or lower. The pour point can be determined by, for example, JIS K 2269. The pour point as described in the present specification is a value determined by JIS K 2269.

The viscosity of the medium oil of the present invention is not particularly limited, but preferably is 0.05 to 10 cP at the reaction temperature. If the viscosity greatly exceeds 10 cP, the movement velocity (that is, the flow rate) of the raw gas and the product dissolved in the liquid phase of the slurry-bed reaction layer is lowered, and further the gas holdup and the total surface area of bubbles are decreased due to the increase of the bubble diameter, thereby resulting in reduction of the reaction efficiency. Also, in the case of an exothermic reaction such as DME synthesis, a heat exchanger is installed in the reactor to remove heat the reactor. In this case, the heat transfer coefficient decreases when the viscosity of the medium oil is increased, which requires increase of the heat transfer surface. When the viscosity of the medium oil of the present invention is far below 0.05 cP, the catalyst becomes to be easily precipitated and becomes poorly dispersed. Accordingly, the extent of the contact between the catalyst and the raw gas become poor and the reaction efficiency may be sometimes lowered. Such viscosity can be determined, for example, by calculating the kinematic viscosity and the specific gravity of the medium oil after measuring the kinematic viscosity and the specific gravity. In the present specification, the viscosity was determined by the method described above.

The content of sulfur in the medium oil is preferably several ppms or less and, more preferably 1 ppm or less. If the content of the sulfur exceeds the above range, the catalyst may be poisoned by the sulfur and may be deactivated.

The 50% distillation point (namely, the temperature at which 50% of the oil evaporates under normal pressure) of the medium oil according to the present invention is preferably 230° C. or higher. If the 50% distillation point is lower than the above temperature, and if the amount of the evaporated oil is large under a condition of the reaction temperature and pressure, it is sometimes necessary to increase the capacity of the trap for the evaporated medium oil provided downstream of the reactor, thus to cause the plant cost to be increased.

Among other physical properties of the medium oil to affect the reaction, there is solubility or velocity of dissolution of the raw material, the product and the reaction intermediate of the reaction. For example, for the synthesis of dimethyl ether, the solubility and the dissolution velocity of the raw material such as carbon monoxide or hydrogen, the reaction intermediate such as methanol or water, and the product such as dimethyl ether or carbon dioxide, belong to the physical properties of the medium oil to affect the reaction. If the solubility or the dissolution velocity of the raw material to the medium oil is low, the efficiency of the raw material to reach the catalyst and then to be converted is reduced. And, if the solubility of the product such as dimethyl ether or carbon dioxide is high, the reaction on the catalyst to produce dimethyl ether or carbon dioxide is difficult to progress. In addition, it is desirable that water or methanol as the reaction intermediate compound reaches an activation site of next to the catalyst site immediately after generation thereof and to be converted. The medium oil of the present invention can satisfy the above requirements with regard to the solubility and the dissolution velocity.

The medium oil of the present invention is a medium oil used in the slurry-bed reaction procedure. Such slurry-bed reaction procedure is not particularly limited as far as it conducts the reaction in the catalyst slurry as a mixture of a solid catalyst and a medium oil and includes, for example, the slurry-bed reaction procedure to synthesize an alternative organic compound (that is, a hydrocarbon) and/or an oxygen-containing organic compound from the raw gas material comprising the organic compound (that is, hydrocarbon) and/or carbon monoxide and hydrogen.

The medium oil of the present invention is most preferably applied to the slurry-bed reaction procedure to synthesize the oxygen-containing compound from the raw material containing carbon monoxide and hydrogen. Examples of such oxygen-containing organic compound includes, but is not limited to, ethers such as dimethyl ether, methyl tert (tertiary)-butylether, ethyl tert-butylether or tert-amyl methyl ether; alcohols such as methanol or ethanol; dimethyl carbonate, acetaldehyde, carboxylic acid such as acetic acid; or dimethoxy methane or dimethoxy ethane. The medium oil of the present invention can be further employed in the synthesis of olefins such as propylene or ethylene, or of hydrocarbons such as gasoline components. Such synthesis includes the synthesis of the hydrocarbon or the oxygen-containing organic compound as a reaction intermediate other than the hydrocarbon or the oxygen-containing organic compound as a final product.

As the process for preparing dimethyl ether of this invention, any processes for preparing dimethyl ether conventionally known can be used, except that the medium oil of the present invention is employed. In other words, by passing the raw gas containing carbon monoxide and hydrogen through the catalyst slurry comprising a mixture of the medium oil of the present invention, a catalyst for synthesis of methanol, a methanol dehydration catalyst or a methanol shifting and dehydration catalyst, obtained is dimethyl ether. Additionally, the process of the present invention is of course applied to a method using a catalyst having three functions of such as methanol synthesis, dehydration and shifting. The raw gas material can be supplied by gasification of coal or reforming of methane. The reaction temperature preferably ranges from 150° C. to 400° C. and more preferably from 250° C. to 300° C. Also, the reaction pressure preferably ranges from 1 to 15 MPa and more preferably from 3 to 7 MPa. Moreover, the amount of the catalyst in the medium oil preferably ranges from 1 to 50% by weight and more preferably from 10 to 30% by weight.

In the process for preparing dimethyl ether according to the present invention, the methanol synthesis catalyst includes known methanol catalysts, for example, a catalyst represented by a composition formula: Cu—Zn-M-O (wherein M represents any one or more metallic atoms selected from a group consisting of aluminum, silicon, titanium, zirconium, chromium, cerium and gallium).

In the process for preparing dimethyl ether according to the present invention, example of the methanol dehydration catalyst includes a known methanol dehydration catalyst comprising alumina as the main component or a dehydration catalyst comprising silica, silica•alumina or zeolite as the main component.

In the process for preparing dimethyl ether according to the present invention, example of the shift catalyst includes copper, zinc, iron and chromium.

In the process for preparing dimethyl ether according to the present invention, the methanol dehydration/shift catalyst can be used instead of a combination of such methanol dehydration catalyst and the shift catalyst. The methanol dehydration/shift catalyst is a catalyst with both of methanol dehydrating function and methanol shifting function and, for example, a catalyst comprising the methanol dehydration catalyst with addition of shifting function by copper, that is, the methanol dehydration/shift catalyst comprising copper oxides, and alumina as the main component (composition formula: Cu—Al—O); the methanol dehydration/shift catalyst comprising copper oxides and silicon oxides (composition formula: Cu—Si—O); or the methanol dehydration/shift catalyst comprising copper oxides, silica and alumina (composition formula: Cu—Si—Al—O). The product by the method according to the present invention can be separated and purified by a conventional method.

As the process for preparing a mixture comprising dimethyl ether and methanol according to the present invention, any conventionally known processes for preparing the mixture comprising dimethyl ether and methanol can be used, except that the medium oil of the present invention is employed. In other words, by passing the raw gas containing carbon monoxide and hydrogen through the catalyst slurry comprising a mixture of the medium oil of the present invention, a catalyst for synthesis of methanol, a methanol dehydration catalyst or a methanol shifting and dehydration catalyst, obtained is the mixture comprising dimethyl ether and methanol. In addition, the process of the present invention is of course applied to a method using a catalyst having three functions of such as methanol synthesis, dehydration and shift. The raw gas material, the methanol synthesis catalyst, the methanol dehydration catalyst and the methanol shifting and dehydration catalyst used in the process for preparing the mixture described above can be the same to those used in the process for preparing dimethyl ether described above. However, in the case of the process for preparing the mixture comprising dimethyl ether and methanol, it is preferable to employ the silica or the silica and alumina based methanol dehydration catalyst and the sifting catalyst with the same base; or the methanol dehydration/shift catalyst comprising silica as the main component; or the methanol dehydration/shift catalyst comprising silica and alumina as the main components.

The following experimental examples are for illustrating the present invention without limitation.

Example 1

{Purification of the Medium Oil of the Present Invention}

By conducting polymerization of 1-decene as a raw material in the presence of an aluminum chloride catalyst and water as an a promoter at −20 to 30° C. and saturation with addition of hydrogen then purification, obtained was a product, that is, the medium oil. Physical properties thereof were adjusted depending on the composition of the raw material, the polymerization temperature and/or conditions for the purification (that is, distillation). The obtained medium oil was subjected to determination of chemical properties by the following means.

In particular, the weight average molecular weight of the medium oil was measured by means of mass spectroscopy and gel-permeation chromatography. The vapor pressure was determined using a boiling point procedure by means of an ebulliometer. % $C_P$ as a percentage of paraffinic carbon atoms to the total carbon atoms was determined by the n-d-M method (ASTM D 3238). The viscosity at 260° C. was measured using kinematic viscosity and specific gravity. Lastly, the pour point was determined by JIS K 2269. As a result, it was identified that the produced α-olefin oligomer has a structure represented by the above formula (1), the weight average molecular weight of 427, the vapor pressure of 1.2 kPa at 260° C. and the pour point of −70° C., in addition to, % $C_P$, viscosity, the pour point and other physical properties being within the desirable ranges described above. Also, the content of sulfur in the obtained medium oil was equal to or less than 1 ppm.

This medium oil is referred to as the medium oil of Example 1.

Comparative Examples 1 and 2

{Purification of the Medium Oil as Comparative Examples}

By conducting polymerization of a mixture of n-butene and isobutene (containing a trace amount of butane, etc.) as a raw material in the presence of an aluminum chloride catalyst and water as a promoter at −20 to 30° C. and saturation with addition of hydrogen then purification, obtained was a product. Physical properties thereof were adjusted depending on the composition of the raw material, the polymerization temperature and/or conditions for the purification (that is, distillation). The product was subjected to separation of both aliquots comprising one medium oil having the weight average molecular weight of 300 and the other medium oil having the weight average molecular weight of 470. Chemical properties for these medical oils were determined by the same procedures illustrated in Example 1. It was found that the medium oil having the weight average molecular weight of 300 has the vapor pressure of 27 kPa at 260° C. and the pour point of −40° C., while the medium oil having the weight average molecular weight of 470 showing the vapor pressure of 2.0 kPa at 260° C. and the pour point of −20° C.

Hereinafter, the medium oil having the weight average molecular weight of 300 is referred to as the medium oil of Comparative Example 1, and the medium oil with the weight average molecular weight of 470 is referred to as the medium oil of Comparative Example.

Example 2

(Synthesis of Dimethyl Ether/Methanol and Evaluation of Synthesis Efficiency)

Figure 14:
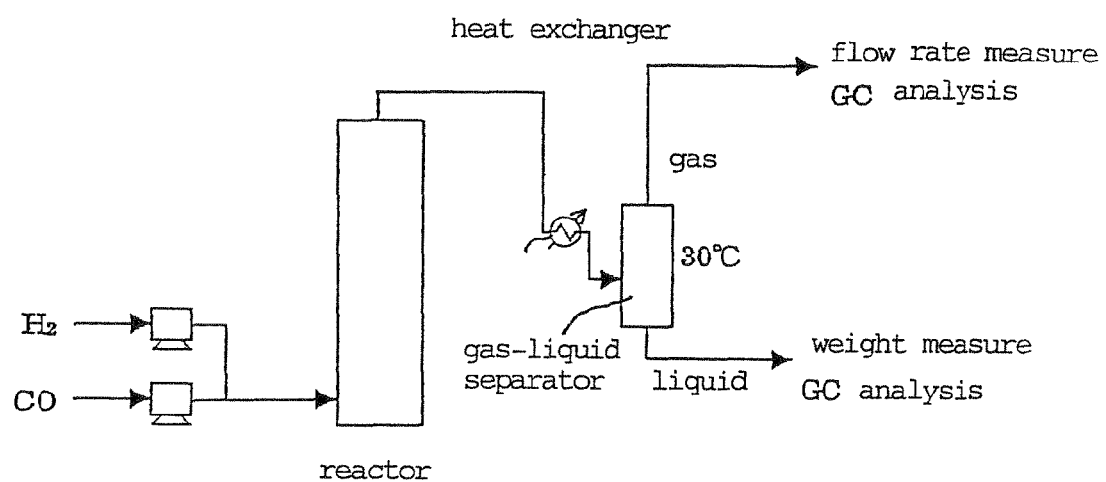
FIG. 14 is a construction diagram for explaining a synthesis apparatus for synthesizing dimethyl ether.

FIG. 14 shows a constructional scheme of a synthesis apparatus illustrating the synthesis of dimethyl ether.

In a reactor of the synthesis apparatus, added were 1552 g of the medium oil of Example 1, then 259 g of a methanol synthesis catalyst based on copper-zinc-alumina (CuO/ZnO/$Al_2O_3$: 31/16/53) and 129 g of an alumina based methanol dehydration/shift catalyst (CuO/$SiO_2 \cdot Al_2O_3$) to form a slurry-bed [weight ratio of the methanol synthesis catalyst and the methanol dehydration/shift catalyst (methanol synthesis catalyst:methanol dehydration/shift catalyst)=2:1, and the total weight of the methanol synthesis catalyst and the methanol dehydration/shift catalyst being 388 g], a slurry was prepared by mixing the above and then the reactor was closed. By passing the raw gas material [carbon monoxide: 18.11 NL/min, hydrogen gas: 18.11 NL/min, the amount to be passed was determined using a mass flowmeter] through the slurry under stirring the slurry in the reactor, performed was the synthesis of dimethyl ether. The reaction temperature was 260° C. and the reaction pressure was 5 MPa. Also, in order to bring the catalyst a suitable reduction state before performing the synthesis, carried out was a preliminary reduction operation by passing a 1:1 mixed gas of $H_2$/CO at about 220° C. for 12 hours under a pressure of 0.5 MPa through the slurry.

In the above dimethyl ether synthesis process, the gas which passed through the reactor (the produced gas) was cooled to about 30° C. in the heat exchanger, then separated into a liquid phase containing methanol and water and a vapor phase containing unreacted gas components, carbon dioxide and dimethyl ether in the vapor-liquid separator. The liquid recovered from the vapor-liquid separator was discharged out of the vapor-liquid separator through a vacuum valve, was brought to normal pressure to vaporize $CO_2$ and DME, and MeOH and $H_2O$ were obtained as a liquid. The gas generated during the pressure reduction (not shown in FIG. 14) was metered for the flow rate by a gas-meter and then subjected to an analysis for the composition by a gas chromatograph. For the obtained liquid, after determining the weight of the liquid by sampling for a fixed period of recovery time, the analysis of composition was performed by means of a gas chromatograph. The gas separated from the vapor-liquid separator was metered for the flow rate by a gas-meter and then subjected to an analysis for the composition by a gas chromatograph. For each of the gas separated from the vapor-liquid separator, the gas generated during the pressure reduction of the liquid and the residual liquid after the pressure reduction, the flow rate of each component was calculated and then added together, from which the composition of the generated gas was determined. From the above results, carbon monoxide conversion (unit=%) and yield of dimethyl ether (unit=mol/g of catalyst and time (hr)) were calculated by the following equation:

$$\text{Conversion of carbon monoxide} = 100 \times (V_{in} - V_{out})/V_{in}$$

wherein $V_{in}$ represents the flow rate of carbon monoxide in the raw gas material while $V_{out}$ is the flow rate of carbon monoxide in the produced gas. Yield of dimethyl ether=$W_{DME}/W_{cat}$ wherein $W_{DME}$ represents the amount of dimethyl ether per hour while $W_{cat}$ is the weight of catalyst.

Furthermore, (1) Conversion of carbon monoxide (CO) 100 hours after the reaction was started (unit=%); (2) Conversion of carbon monoxide (CO) 300 hours after the reaction was started (unit=%); (3) Yield reduction of dimethyl ether (DME) (unit=%); and (4) Amount of medium oil volatilized 300 hours after the reaction was started (unit=g) were investigated. Also, the yield reduction of dimethyl ether of above (3) means a reduction ratio of [yield of dimethyl ether 300 hours after the reaction was started (B)] to [yield of dimethyl ether 100 hours after the reaction was started (A)] represented by [(A−B)/A].

Comparative Examples 3 and 4

The procedure illustrated in Example 2 was repeated except the use of the medium oils of Comparative Example 1 and 2 instead of the medium oil of Example 1.

{Results of Example 2 and Comparative Examples 3 and 4}

The results of the above (1) to (4) obtained from Example 2 and Comparative Examples 3 and 4 are listed in Table 7.

TABLE 7

|  | Example 2 | Comparative Example 3 | Comparative Example 4 |
| --- | --- | --- | --- |
| Types of medium oil | Medium oil of Example 1 | Medium oil of Comparative Example 1 | Medium oil of Comparative Example 2 |
| (1) CO conversion after 100 hours (%) | 54.0 | 54.5 | 46.1 |
| (2) CO conversion after 300 hours (%) | 51.3 | 51.0 | 40.2 |
| (3) Yield reduction of DME (%) | 5.0 | 6.4 | 12.8 |
| (4) Amount of medium oil volatilized after 300 hours (%) | 9.6 | 272 | 12.2 |

As shown in the above Table 7, it was found that when the medium oil of the present invention obtained from Example 1 was used, not only it was possible to maintain a high rate of synthesis of dimethyl ether for a long time, but also, as compared to the medium oil obtained from Comparative Example 1, there was substantially no reduction of the amount of the medium oil for a long time and a stable synthesis for a long time was ensured.

More specifically, in the case of Comparative Example 3 (using the medium oil of Comparative Example 1), the CO conversion and the yield reduction of DME, that is, deterioration along lapse of time, were substantially equal to those of the medium oil of Example 1. However, the amount of the medium oil volatilized was 20 times or more than that of the medium oil of Example 1. The molecular weight distribution of the medium oil volatilized in Comparative Example 3 extended near to the molecular weight distribution of a fraction separated by distillation, and, from the results of GC-MS analysis for the above volatilized medium oil, it was suggested that thermal decomposition was occurring in quaternary carbon moiety.

In Comparative Example 4 (using the medium oil from Comparative Example 2), the volatilized amount of the medium oil was substantially equal to that of the medium oil of Example 1, whereas CO conversions at an initial period and after stabilization were lowered and the DME yield reduction was increased. It was suggested that this was due to a high viscosity of the medium oil of Comparative Example 2 and low solubility for the raw gas material. The molecular weight distribution of the medium oil volatilized in Comparative Example 2 also extended near to the molecular weight distribution of the fraction separated by distillation, and, from the results of GC-MS analysis for the above volatilized medium oil, it was suggested that thermal decomposition was occurring in quaternary carbon moiety.

As a result of mass spectroscopic analysis, the medium oil obtained from Example 1 comprised trimer and tetramer as main components and trace amount of dimer, pentamer and hexamer. For the volatilized medium oil, trimer was the main component and minor components were trace amount of dimer and tetramer, while no thermal decomposition products were included therein.

In addition, all of the medium oils of Example 2 and Comparative Examples 3 and 4 had the reduced amount of volatilized medium oil compared to the volatilized amount calculated from the vapor pressure at 260° C. This is because the temperature of the top portion of the reactor is kept at about 110° C., and only the medium oil flowing out in a gaseous or mist state passed through the top portion of the reactor.

From the medium oil volatilized out of the reactor, typically a fraction of the pure medium oil is separated and then returned into the reactor by means of a high-pressure pump to keep a constant concentration of the catalyst. However, the above recovery operation was not conducted in Example 2 and Comparative Example 4 since the volatilized amounts of the medium oils were small. In Comparative Example 3, it was expected that the volatilized amount was increased by circulation of the medium oil having low-boiling fraction, thus it was compensated with the fresh medium oil having the same composition by supplying the corresponding weight.

What is claimed is:

1. A process for preparing dimethyl ether comprising passing a raw gas containing carbon monoxide and hydrogen through a catalyst slurry containing a mixture comprising (a) a medium oil comprising, as a main component, a branched, saturated aliphatic hydrocarbon having 16 to 50 carbon atoms, 1 to 7 tertiary carbon atoms, 0 quaternary carbon atom, and 1 to 16 carbon atoms in the branched chains bonded to the tertiary carbon atoms; and at least one of the tertiary carbon atoms being bonded to hydrocarbon chains with a chain length having 4 or more of carbon atoms in three directions; (b) a methanol synthesis catalyst; (c) a methanol dehydration catalyst; and (d) a methanol shift catalyst or a methanol dehydration/shift catalyst.

2. A process for preparing a mixture of dimethyl ether and methanol comprising passing a raw gas containing carbon monoxide and hydrogen through a catalyst slurry containing a mixture comprising (a) a medium oil comprising as a main component, a branched, saturated aliphatic hydrocarbon having 16 to 50 carbon atoms, 1 to 7 tertiary carbon atoms, 0 quaternary carbon atom, and 1 to 16 carbon atoms in the branched chains bonded to the tertiary carbon atoms; and at least one of the tertiary carbon atoms being bonded to hydrocarbon chains with a chain length having 4 or more of carbon atoms in three directions; (b) a methanol synthesis catalyst; (c) a methanol dehydration catalyst; and (d) a methanol shift catalyst or a methanol dehydration/shift catalyst.

3. The process according to claim 1, wherein the branched, saturated aliphatic hydrocarbon has 20 to 40 carbon atoms and 1 to 4 tertiary carbon atoms.

4. The process according to claim 1, wherein the branched, saturated aliphatic hydrocarbon is represented by formula (I):

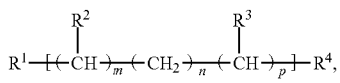 (I)

wherein $R^1$, $R^2$ and $R^4$ are independently an n- or iso-alkyl group having 4 to 16 carbon atoms, $R^3$ is an n- or iso-alkyl group having 1 to 3 carbon atoms, m is an integer of 1 to 7, n is an integer of 0 to 37, and p is an integer of 0 to 12, provided that —(CR$^2$H)—, —(CH$_2$)— and —(CR$^3$H)— are bonded in any order and the total numbers of each unit are m, n and p, respectively.

5. The process according to claim 1, wherein the branched, saturated aliphatic hydrocarbon is an α-olefin polymer.

6. The process according to claim 1, wherein the medium oil has a pour point of −10° C. or lower.

7. The process according to claim 2, wherein the branched, saturated aliphatic hydrocarbon has 20 to 40 carbon atoms and 1 to 4 tertiary carbon atoms.

8. The process according to claim 2, wherein the branched, saturated aliphatic hydrocarbon is represented by formula (I):

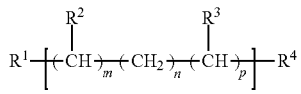 (I)

wherein $R^1$, $R^2$ and $R^4$ are independently an n- or iso-alkyl group having 4 to 16 carbon atoms, $R^3$ is an n- or iso-alkyl group having 1 to 3 carbon atoms, m is an integer of 1 to 7, n is an integer of 0 to 37, and p is an integer of 0 to 12, provided that —(CR$^2$H)—, —(CH$_2$)— and —(CR$^3$H)— are bonded in any order and the total numbers of each unit are m, n and p, respectively.

9. The process according to claim 2, wherein the branched, saturated aliphatic hydrocarbon is an α-olefin polymer.

10. The process according to claim 2, wherein the medium oil has a pour point of −10° C. or lower.

* * * * *